United States Patent
Stewart et al.

(10) Patent No.: US 7,545,907 B2
(45) Date of Patent: Jun. 9, 2009

(54) METHODS AND APPARATUS FOR OBTAINING LOW-DOSE IMAGING

(75) Inventors: Alexander Stewart, Waltham, MA (US);
 Martin Stanton, Concord, MA (US);
 Edward Bullard, London (GB)

(73) Assignee: Dexela Limited, London (GB)

( * ) Notice: Subject to any disclaimer, the term of this patent is extended or adjusted under 35 U.S.C. 154(b) by 0 days.

(21) Appl. No.: 11/595,664

(22) Filed: Nov. 9, 2006

(65) Prior Publication Data

US 2007/0242797 A1    Oct. 18, 2007

Related U.S. Application Data

(60) Provisional application No. 60/735,140, filed on Nov. 9, 2005.

(51) Int. Cl.
 *A61B 6/04* (2006.01)
(52) U.S. Cl. .................................. 378/37; 378/108
(58) Field of Classification Search ............. 378/95–96, 378/97, 108–112, 60, 37, 4
See application file for complete search history.

(56) References Cited

U.S. PATENT DOCUMENTS

| | | | |
|---|---|---|---|
| 5,949,811 A * | 9/1999 | Baba et al. | 378/108 |
| 6,744,848 B2 * | 6/2004 | Stanton et al. | 378/55 |
| 2001/0038681 A1 * | 11/2001 | Stanton et al. | 378/108 |
| 2003/0095624 A1 | 5/2003 | Eberhard et al. | |
| 2004/0101095 A1 * | 5/2004 | Jing et al. | 378/37 |
| 2005/0113681 A1 | 5/2005 | DeFreitas et al. | |
| 2005/0226375 A1 | 10/2005 | Eberhard et al. | |

* cited by examiner

*Primary Examiner*—Hoon Song
(74) *Attorney, Agent, or Firm*—Wolf, Greenfield & Sacks, P.C.

(57) ABSTRACT

In one aspect, a method of obtaining projection data of an object from a plurality of view angles with respect to the object is provided. The method comprises acts of providing radiation, at each of the plurality of view angles, to an exposure area in which the object is positioned, controlling a radiation energy of the radiation provided at each of the plurality of view angles such that the respective radiation energy is different for at least two of the plurality of view angles, and detecting at least some of the radiation passing through the exposure area at each of the plurality of view angles to obtain the projection data.

24 Claims, 6 Drawing Sheets

METHODS AND APPARATUS FOR OBTAINING LOW-DOSE IMAGING

RELATED APPLICATION

This application claims priority under 35 U.S.C. § 119(e) to U.S. Provisional Application Ser. No. 60/735,140, entitled "Planar Imaging Methods and Techniques," filed on Nov. 9, 2005, which is herein incorporated by reference in its entirety.

FIELD OF THE INVENTION

The present invention relates to radiation imaging, and more particularly, to obtaining projection data of an object by exposing the object to radiation from a plurality of view angles.

BACKGROUND OF INVENTION

Imaging apparatus that utilize relatively high energy radiation such as x-ray and gamma rays are widely used to obtain images of subject matter more or less opaque to electromagnetic energy in the visual spectrum. For example, x-ray imaging technology has been employed in a wide range of applications from medical imaging to detection of unauthorized objects or materials in baggage, cargo or other containers. X-ray imaging typically includes passing high energy radiation (i.e., x-rays) through an object to be imaged. X-rays from a source passing through the object interact with the internal structures of the object and are altered according to various characteristics of the material (e.g., transmission, scattering and diffraction characteristics, etc.) which the x-rays encounter. By measuring changes in the X-ray radiation (e.g., attenuation, modifications to the energy spectrum, scatter angle, etc.) that exits the object, information related to characteristics of the material, such as the density distribution, may be obtained.

Computer tomography (CT) techniques involve capturing transmitted x-ray information from numerous angles about an object being imaged, to reconstruct a three-dimensional (3D) volume image of the object. The data obtained from each view angle is referred to as projection data or view data and is indicative of the absorption characteristics of the object in directions related to the respective view angle. However, CT imaging often involves obtaining hundreds or thousands of projections to form a 3D reconstruction of the projection data, thus requiring the object to be exposed to relatively large doses of x-ray radiation and/or over applications having particular safety and/or time constraints. For example, when imaging human tissue, and/or when the imaging procedure is performed on a routine or frequent basis (such as is often the case in mammography), dose levels and/or exposure times used in conventional CT imaging may exceed that which is more desirable.

To reduce a patient's exposure during breast imaging procedures (e.g., imaging of the human female breast), conventional mammography is often performed by obtaining only a pair of two-dimensional (2D) radiographic images of the breast (i.e., each image is reconstructed from a single projection of the breast), typically acquired at approximately complementary angles to one another. However, the superposition of structure within the breast that occurs when 3D structure is projected onto two dimensions often obscures the true nature of the structure. This superposition of structure may make it difficult to identify or detect tissue anomalies. For example, distinct structure in 3D that overlaps in 2D may make it difficult to distinguish cancerous subject matter from benign subject matter within the breast.

In conventional mammography, the inability to ascertain the true nature of breast structure may result in both significant false negative and false positive rates, leading to potential missed early stage cancers in the case of the former, or unnecessary trauma to the patient and/or unnecessary hospital visits, surgical procedures, etc., in the case of the latter. Similarly, other imaging procedures that solve radiation dose and/or time considerations by acquiring only a limited number of 2D radiographic images are vulnerable to the same risks of misdiagnosis.

SUMMARY OF THE INVENTION

Some embodiments according to the present invention include a method of obtaining projection data of an object from a plurality of view angles with respect to the object, the method comprising acts of providing radiation, at each of the plurality of view angles, to an exposure area in which the object is positioned, controlling a radiation energy of the radiation provided at each of the plurality of view angles such that the respective radiation energy is different for at least two of the plurality of view angles, and detecting at least some of the radiation passing through the exposure area at each of the plurality of view angles to obtain the projection data.

Some embodiments according to the present invention includes an apparatus for obtaining projection data of an object from a plurality of view angles with respect to the object, the apparatus comprising a radiation source adapted to provide radiation to an exposure area in which the object may be positioned, the radiation source being moveable to provide the radiation to the exposure area from each of the plurality of view angles, an exposure controller coupled to the radiation source, the exposure controller adapted to control a radiation energy of the radiation provided by the radiation source at each of the plurality of view angles such that the respective radiation energy is different for at least two of the plurality of view angles, and at least one detector positioned to detect at least some of the radiation passing through the exposure area at each of the plurality of view angles to obtain the projection data.

DETAILED DESCRIPTION

Figure 1:
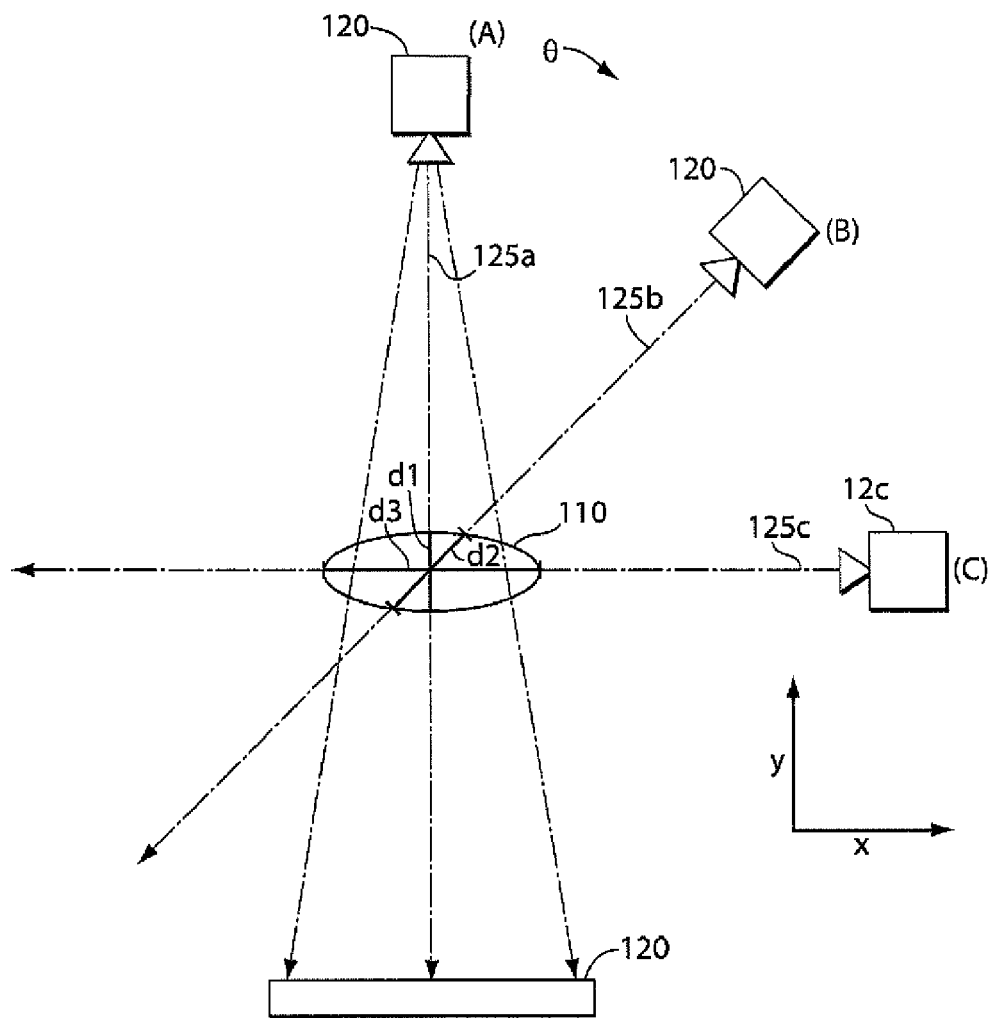
FIG. 1 is a geometric illustration aid in explanation of Applicant's insight that variations in object thickness may result in variation in subject dose when projection data is obtained from a plurality of view angles of a non-uniform object.

As discussed above, conventional approaches to providing generally low-dose radiation imaging suffer from images that provide confusing representations of internal structures of an object due, at least in part, to the projection of three-dimensional structure onto one or more two-dimensional images. The resulting superposition of distinct structure located at different levels in 3D makes discerning the actual structure in a 2D representation difficult, rendering conventional imaging procedures vulnerable to errors in diagnosis. Applicant has appreciated that a number of projections obtained using variable radiation doses may be appropriate for acquiring projection data that may be reconstructed to form 3D images, while still respecting a relatively low dose budget (e.g., dose budgets suitable for mammography or other tissue exposures that are generally dose limited due to safety concerns). U.S. Pat. No. 6,744,848 (hereinafter the '848 patent), which is herein incorporated by reference in its entirety, describes various methods and apparatus for obtaining 3D images in a relatively low dose environment.

Applicant has appreciated that, in some circumstances, the subject dose received by a patient may be varied with respective to the view angle at which projection data was obtained, particularly when the object being imaged is non-uniform in shape. The term "subject dose" refers herein to the amount of radiation absorbed by an object being exposed to radiation, and may be an important component in assessing the potential harm of the x-ray imaging process. In particular, radiation that merely passes through tissue is significantly less harmful to the subject than radiation absorbed by the tissue. Accordingly, reducing the amount of radiation absorbed by tissue is a significant concern in medical imaging, and particularly in procedures that are performed regularly and/or are sensitive to radiation dose (e.g., breast imaging).

The absorption of radiation is an exponential function of the thickness of material that the radiation must penetrate (and a function of the material properties). For example, the attenuation of radiation through matter can be described generally according to the characteristic attenuation function:

$$I = I_0 e^{-\beta z} \quad (1).$$

where $I_0$ is the intensity of the radiation emitted from a radiation source before penetrating the material, I is the intensity of radiation having penetrated the material through a thickness z, and, $\beta$ is a coefficient incorporating both a material specific linear absorption coefficient, $\mu$ and the energy of the radiation $\lambda$ (which is related to wavelength). The term "intensity," with respect to radiation, refers to the amount of radiation present at a given surface or passing through a given volume during a given interval of time, and is thus a measure of radiation flux. Thus, the difference between I and $I_0$ is indicative of the subject dose (i.e., $I_0 - I$ is indicative of how much radiation the object absorbed). Inspection of Equation 1 reveals that as z increases, the difference between I and $I_0$ likewise increases. That is, when all other variables are held constant, the subject dose increases as the thickness of the material being penetrated increases.

Accordingly, in imaging procedures that expose an object at multiple angles, the relative amount of radiation absorbed by the object will vary with view angle for non-uniform objects, resulting in increased subject dose levels at view angles wherein impinging radiation must penetrate increased thicknesses of material. Applicant has appreciated that, due at least in part to the increased transmissivity of higher energy radiation, the subject dose received by a non-uniform object may be maintained or decreased by varying the radiation energy (not radiation intensity) of the radiation to which the object is exposed. In particular, as the thickness of an object increases at certain view angles, the radiation energy may be increased to maintain the amount of absorption within a suitable range, while maintaining image quality. As one result, the data desired for calculating a 3D representation of the object may be obtained while maintaining or decreasing the subject dose of the object. It should be appreciated that the term "radiation energy" and "radiation intensity" refer to separate and distinct properties of the radiation. The term radiation energy is related to the wavelength of the photons of the radiation, while the term intensity is related to the radiation flux.

In one embodiment, projection data is obtained from a plurality or view angles (i.e., at a plurality of different orientations with respect to an object). At each of the plurality of view angles, a radiation energy is selected based, at least in part, on a thickness of the object in a direction related to the respective view angle. In this manner, as the thickness of the object changes, the radiation energy may be varied to control the absorption of radiation while substantially maintaining image quality, thus limiting the subject dose received to desired levels.

In general, radiation provided for the purpose of obtaining projection data of an object is polychromatic. That is, rather than the radiation having a single energy (monochromatic), radiation emitted from a radiation source will have an energy distribution comprising multiple energies. For example, radiation used in imaging exposures is often generated by directing an electron beam (e-beam) to strike a target surface. Common target materials include tungsten, molybdenum, rhodium, etc. The interaction of the e-beam with the target surface results in the emission of radiation comprised of multiple energies that are dependent on the target material type and the energy of the e-beam. That is, each target material will emit a characteristic energy distribution, or spectrum, in response to an impinging e-beam.

An e-beam used to bombard a target to generate radiation is often itself generated in a vacuum tube, and has an energy proportional to a voltage potential between a cathode and anode (the target material) of the vacuum tube. As the energy in the e-beam increases, so does the energy of the radiation emitted by the target, as discussed in further detail below. Thus, a target material will emit radiation having a characteristic spectrum that depends both on the material type being used and on the energy in the e-beam impinging on its surface. In the context of e-beam technology, varying the radiation energy typically involves varying the energy level of the e-beam to correspondingly vary the characteristic spectrum.

As a general matter, varying the radiation energy refers to varying the energy content of the energy distribution (i.e., varying the content of the energy spectrum). For example, increasing the radiation energy typically involves shifting the distribution of energies to higher frequencies. For example, if the energy in the e-beam is increased, the energy distribution of the radiation emitted by the target in response to the impinging e-beam will experience a corresponding shift to higher frequencies. That is, portions of the energy spectrum of radiation emitted from a target, increases in intensity and shifts toward higher frequencies (shorter wavelengths) when the energy of the e-beam used to bombard the target is increased. It should be appreciated that the energy distribution may not shift uniformly (e.g., characteristic energy peaks for various target materials may increase in intensity but not shift in frequency as a function of e-beam energy), but the sum of the energies in the energy distribution will vary in proportion to the e-beam energy.

Accordingly, the term "radiation energy" refers generically to an indicator of the energy distribution as a whole. For example, with monochromatic radiation, the radiation energy may indicate the wavelength of the emitted radiation. With polychromatic radiation, the radiation energy may indicate the energy distribution in any characteristic manner, for example, the radiation energy may refer to a mean energy, a median energy, a predominant energy, a sum of the energy distribution, or other indicator characteristic of the energy distribution. Therefore, increasing or decreasing the radiation energy for polychromatic radiation refers to increasing or decreasing one or more characteristics of the energy distribution and/or increasing or decreasing the energy distribution as a whole.

It should be appreciated that while the terms radiation intensity and radiation energy refer to different characteristics of radiation, they are not entirely unrelated. In particular, increasing the intensity of radiation while maintaining the same radiation energy will increase the total energy of the radiation. That is, providing more radiation at any particular radiation energy will naturally increase the total energy of the radiation. Accordingly, the term "total energy" refers to the energy present in radiation emitted over some interval of time, such as during an exposure, and takes into consideration both the radiation energy and the radiation intensity of the radiation. It should be appreciated that the radiation intensity may be decreased and the radiation energy increased while maintaining the same total energy in the radiation provided for an exposure (and likewise for an increase in radiation intensity and a decrease in radiation intensity), as the total energy is comprised of both components. Accordingly, the total energy incident on an object may be increased while the subject dose actually decreases, due to the increased transmissivity of the object at the higher energy.

As discussed above, projection data may be obtained from an object by exposing the object to relatively high energy radiation and detecting the radiation that passes through the object. By comparing the known intensity of the radiation incident on the object with the detected intensity of the radiation exiting the object, information about the absorption characteristics (e.g., the density) of the tissue may be computed. To obtain images having suitable contrast, the difference in intensity between radiation entering and exiting an object must be such that it carries enough information to discriminate between various tissue types. For example, if too much or too little radiation exits the object with respect to the amount of provided radiation, the penetrating radiation will carry insufficient information to distinguish tissue types, resulting in relatively low contrast images.

In particular, considering the limiting cases, if no radiation exits the object because, for instance, the thickness of the material is such that all of the radiation is absorbed and/or the radiation energy is insufficient to fully penetrate the material, no information about the density distribution of the material is obtained. Likewise, if the radiation exits the object substantially unchanged because, for example, the material thickness is such that no appreciable amount of radiation is absorbed and/or the radiation energy is too high, no information about the density distribution of the material is obtained. Between the two extremes, a ratio between impinging and exiting radiation exists that produces optimal contrast information in the exiting radiation.

Higher energy radiation is generally more transmissive than lower energy radiation, thus penetrating matter more readily with a lesser probability of being absorbed. However, when absorbed, higher energy radiation deposits more energy in the absorbing matter, incurring more subject dose per absorbed unit (i.e., per absorbed photon). Fortunately, an appropriate radiation energy for an appropriate material thickness usually may be determined to ensure that exiting radiation carries sufficient information to contrast the different absorption characteristics of the object, while satisfying subject dose requirements. However, a change in the material thickness may disturb the ratio and have a deleterious effect on the contrast information carried by exiting radiation. Thus, in addition to increasing the subject dose of an exposure, increased material thickness may also reduce the information content of radiation exiting the object. Applicant has appreciated that by varying the radiation energy according to view angle, the ratio between impinging and exiting radiation may be maintained to optimize contrast.

Following below are more detailed descriptions of various concepts related to, and embodiments of, methods and apparatus according to the present invention. It should be appreciated that various aspects of the invention described herein may be implemented in any of numerous ways. Examples of specific implementations are provided herein for illustrative purposes only. In addition, the various aspects of the invention described in the embodiments below may be used alone or in any combination, and are not limited to the combinations explicitly described herein.

FIG. 1 illustrates a method and apparatus for obtaining projection data of an object from multiple view angles under relatively low-dose conditions, in accordance with one type of embodiment of the present invention. In FIG. 1, an object 110 is being exposed to radiation at multiple view angles. Object 110 is non-uniform, e.g., object 110 is larger in one dimension than in another. In particular, object 110 has a larger extent in the x-direction than the y-direction. Object 110 may be, for example, a breast that has been compressed generally in the y-direction in preparation for a breast imaging procedure. As a result, when radiation source 120 is positioned generally in alignment with the y-axis (e.g., at position A), radiation entering object 110 has less subject matter to penetrate before exiting the object than it does when the radiation source is positioned generally in alignment with the x-axis (e.g., at position C).

For example, ray 125a emitted by radiation source 120 at position A must penetrate a distance $d_1$ before exiting the object, while ray 125b provided by radiation source 120 at position B must penetrate a greater distance $d_2$ to exit the object. Thus, photons along ray 125b have a greater likelihood of being absorbed by object 110. As the radiation source rotates about the object from position A to position C, the amount of subject matter rays must penetrate before exiting the object increases (i.e., distance $d_1 < d_2 < d_3$). As a result, if the radiation energy in the radiation is held constant, less of the radiation impinging on object 110 will exit at each increasing angle θ with respect to the y-axis. The view-angle-dependent absorption in FIG. 1 impacts the imaging process in a number of ways. First, the object will be subjected to an increase in subject dose as the radiation source rotates from alignment with the y-axis to alignment with the x-axis. In addition, the information contrast in the radiation that does exit the object to impinge on detector 130 will be reduced as a function of increasing angle θ. Applicant has appreciated that the effects of variations in material thickness can be substantially counter-balanced by varying the radiation energy.

As illustrated in Equation 1 above, the relationship between the intensity of radiation impinging on an object ($I_0$) and the intensity of radiation exiting an object (I) is a function of the thickness z of material through which the radiation penetrates. In addition, the relationship between $I_0$ and I is also a function of radiation energy. In particular, β is a function of radiation energy λ and a material-specific linear absorption coefficient μ that may incorporate various absorption and scattering effects including Thompson scattering, Compton scattering, photoelectric (PE) absorption, pair production, photodisintegration, etc. The radiation energy effects the rate of the exponential decay of the radiation intensity as a function of thickness z. Thus, the intensity of radiation having higher energies will be less effected by increased material thicknesses than the intensity of radiation having lower energies. This energy dependence can be approximated by the expression, $$I(\lambda) = I_0(\lambda) e^{-f(\lambda, \mu) z} \qquad (2).$$

Accordingly, the photon energy of the x-ray radiation impacts the relationship between I and $I_0$ as a function of z. Therefore, approximate or measured values of the material properties of an object being imaged, for example, the known material properties of breast material, may be used to compute radiation energies for various thicknesses z that maintain the difference $I_0-I$ and/or the ratio $I/I_0$ within an acceptable range at respective view angles. Stated differently, variations in subject dose and contrast information caused by changes in material thickness may be reduced and/or eliminated by correspondingly varying the radiation energy.

Accordingly, in FIG. 1, the radiation energy of the radiation provided to the object may be varied as a function of the view angle of the radiation source with respect to the object to account for the increase in object thickness. It should be appreciated that an object being imaged may not vary as uniformly or be as homogeneous as object 110. Thus, as a general matter, the radiation energy applied to an object being imaged may be varied as a function of a thickness of the object in a direction related to the corresponding view angle. In particular, as the amount material in which the radiation must penetrate to exit the object increases, the energy of the radiation may be correspondingly increased to maintain an acceptable level of radiation absorption and/or to maintain sufficient information contrast in the exiting radiation.

The appropriate energy levels at different view angles or thicknesses may be determined either analytically using modeled absorption characteristics, or computed empirically by testing various sample or reference objects, as described in further detail below. In addition, information obtained by monitoring the ratio of I to $I_0$ on successive projections may be used to appropriately adjust the radiation energy in a subsequent exposure at the next view angle. $I_0$ may be measured using the same detector apparatus arranged to collect the projection data, or additional detectors may be arranged to perform measurements on and/or otherwise monitor $I_0$. Alternatively, $I_0$ may be approximated from knowledge of the operating parameters of the radiation source. Measuring and/or otherwise determining the ratio of I to $I_0$ may be achieved in other ways, as the aspects of the invention are not limited in this respect.

Figure 2:
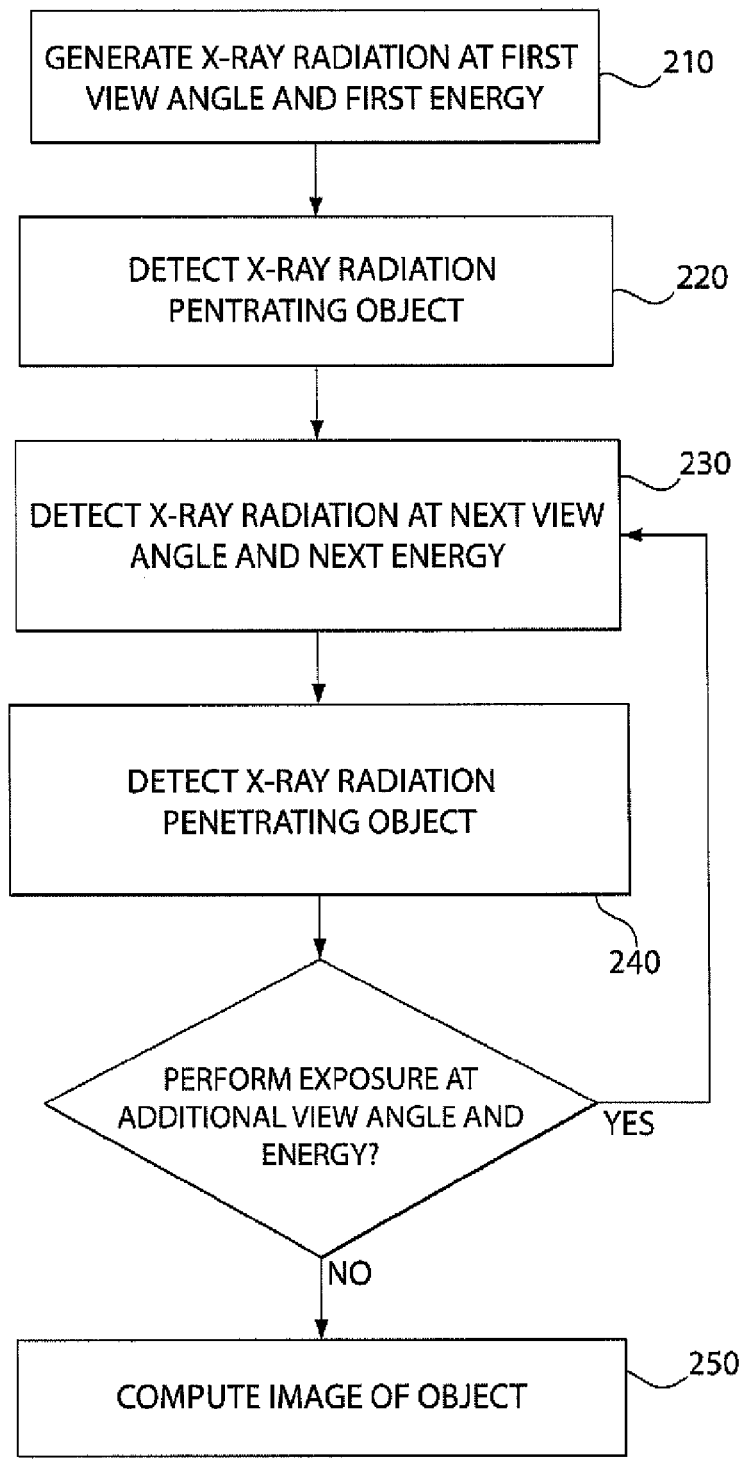
FIG. 2 is a flow chart illustrating a method for obtaining projection data from a plurality view angles using variable radiation energy to compensate for variations in object thicknesses, in accordance with one embodiment of the present invention.

FIG. 2 illustrates a method of performing x-ray imaging using x-ray energy that varies as a function of the view angle of the radiation source with respect to an object being imaged, in view of variations in object thickness in directions related to the corresponding view angle, in accordance with one embodiment of the present invention. Method 200, for example, may be suitable for x-ray imaging procedures having a limited dose budget due to sensitivity of the object (e.g., biological tissue) and/or regularity of the procedure (e.g., routine breast examinations).

In act 210, x-ray radiation is generated and provided to an object being imaged, the x-ray radiation is directed at a first view angle with respect to the object. The x-ray radiation may be provided to form a radiation field such as, for example, a beam that propagates out from a source point in the general shape of a cone to expose an exposure area to the radiation. As such, various rays within the radiation may be propagating in different directions (i.e., depending on the location of the ray within the cone beam). Accordingly, the view angle of the radiation may generally be viewed as the angular orientation of a reference line from the source point through a reference point of the object being imaged (e.g., a center point of the object).

The x-ray radiation at the first view angle is generated at a first radiation energy, the first radiation energy being based, at least in part, on a thickness of the object in a direction related to the first view angle. The first energy may be chosen, for example, such that the amount of x-rays absorbed by the object is below a desired subject dose threshold in view of the particular imaging procedure. In addition, the first energy may be selected such that the ratio of generated x-rays to penetrating x-rays exiting the object provides for sufficient contrast in the resulting image. The x-rays exiting the object may then be detected to acquire information about the material characteristics of the object (act 220). That is, projection data of the object may be acquired corresponding to the first view angle. The projection data may be stored for use in computing one or more images of the internal structure of the object.

In act 230, x-ray radiation is generated and provided to the object at a next view angle and a next energy is selected for the x-ray radiation provided at the next view angle based, at least in part, on the thickness of the object in a direction related to the next view angle. In particular, the next x-ray energy may be varied to account for an increase or decrease in the thickness of the object so as to ensure that the subject dose received by the object does not exceed desired levels and/or to maintain adequate information contrast in the detected x-rays exiting the object. The x-rays penetrating and exiting the object at the next energy may then be detected to acquire projection data related to the material characteristics of the object at the next view angle (act 240). The projection data may be stored for use in computing the one or more images of the internal structure of the object.

In act 250, a determination is made as to whether x-ray radiation is to be generated at another view angle and energy. If an exposure at an additional view angle and energy is desired, then acts 230 and 240 may be repeated. It should be appreciated that x-ray radiation may be provided at any number of view angles and at any number of energies, as the aspects of the invention are not limited in this respect. In addition, while various embodiments may use x-ray radiation, radiation in other portions of the electromagnetic spectrum (e.g., gamma rays) may be used, as the aspects of the invention are not limited in this respect.

If no further exposures are desired, the projection data obtained from the plurality of view angles and energies may be used to compute one or more images of the structure of the object (act 250). For example, the projection data may be reconstructed to form a three dimensional (3D) image of the structure of the object. The projection data may be used in reconstructing an image according to any of various reconstruction methods and algorithms, as the aspects of the invention are not limited in this respect. For example, a 3D image may be computed according to any of the various reconstruction methods described in the '848 patent, or any other suitable reconstruction algorithm configured to transform projection data into image data.

It should be appreciated that various aspects of the invention may be used in combination with techniques described in the '848 patent. For example, varying the radiation as a function of view angle (e.g., to compensate for varying thicknesses of a non-uniform object) may be combined with varying the radiation intensity as a function of view angle to assist in optimizing the exposure procedures. In particular, the radiation intensity and radiation energy may be varied in view of each other to provide an exposure that satisfies both subject dose constraints and desired contrast in the projection data. Other techniques described in the '848 patent and disclosed herein may be used in any combination, as the aspects of the invention are not limited in this respect. For example, projection data obtained using the various techniques described in the '848 patent may be reconstructed in view of the variable radiation energies used at different view angles about the object.

In reconstructing projection data obtained using variable radiation energy at different exposures, it should be appreciated that, since the energy distribution of the radiation flux varies between exposures, the relationship between the fraction of radiation intensity absorbed (and scattered) by the object and the line integrals of the object density between the radiation source and the radiation detector will change between exposures because the mass attenuation coefficients of substances depend upon radiation energy (e.g., as expressed in Equation 2).

The relationship between the projection data and the radiation intensity incident on the radiation detector may also change between exposures of differing radiation energy (e.g., between exposures having different energy distributions or spectra) due to the characteristics of the detector with regard to radiation energy distribution (and the angle of incidence of the radiation upon the detector if this changes between exposures).

In order to process projection data from multiple exposures taken using varying radiation energy distributions, the relationship between projected density and recorded radiation intensity at the detector (equation 2) should be adjusted for each exposure to use the effective mass attenuation coefficient given the radiation energy emitted by the radiation source and the elemental composition of the object (e.g., the atomic make-up of the object).

Methods for processing projection radiation data taking into account the radiation energy distribution to iteratively estimate the mass attenuation coefficient for the volume elements of a reconstruction are described in I A Elbakri, J A Fessler, entitled "Segmentation-free Statistical Image Reconstruction for Polyenergetic X-ray Computed Tomography with Experimental Validation," Phys. Med. Biol., 48(15):2543-78, August 2003. Various of the methods described in the above identified literature may be used to reconstruct projection data obtained using polychromatic radiation energy. However, it should be appreciated that other reconstruction methods may be used, as the aspects of the invention are not limited in this respect.

For some objects of interest, such as soft body tissues like the breast, the elemental composition is comprised mainly of relatively light elements (e.g., of elements having an atomic number <10) distributed fairly uniformly (e.g., the object is of relatively homogenous density). In such cases, the relation between mass attenuation coefficient and radiation energy may be similar throughout the object and one effect of using a higher average radiation energy is that the attenuation coefficients are reduced at higher energy. In this case only a multiplicative correction for the calculated line integrals of object density may need to be applied to correct for the effect of a change in radiation energy distribution between exposures. This may be calculated from the mass-fraction weighted integrals of the elemental mass attenuation coefficients over the radiation energy distributions of each exposure, or calibration images may be taken with a known calibration object of similar elemental composition and thickness to the object (e.g., Plexiglas sheets) covering the range of usable energy distributions for the apparatus, over the range of view angles.

One of these calibration images can be selected for each exposure to give the projected calibration data for a similar thickness at similar radiation energy distribution and source and detector positioning. Since the projected radiation intensity data from the calibration object divided by the radiation intensity data observed or calculated at corresponding locations without an object present gives attenuation measurements, and the line integrals of density may be calculated for the known calibration object density, the effective attenuation coefficients may be calculated using equation 2. It should be appreciated that reconstructing an image from projection data obtained using polychromatic radiation, and/or obtained using different radiation energies for different view angles may be performed in other ways, as the aspects of the invention are not limited in this respect.

As discussed in the '848 patent, radiation exposures may be performed at a number of non-uniformly distributed view angles. For example, the change in angle from one view angle to another may increase as the angle from a reference view angle (e.g., position A in FIG. 1) increases. That is, as a radiation source is rotated about an object from a reference position, the angle between successive exposures may be increased. However, the various view angles selected also may be uniformly distributed, as the aspects of the invention are not limited in this respect.

Figure 3A:
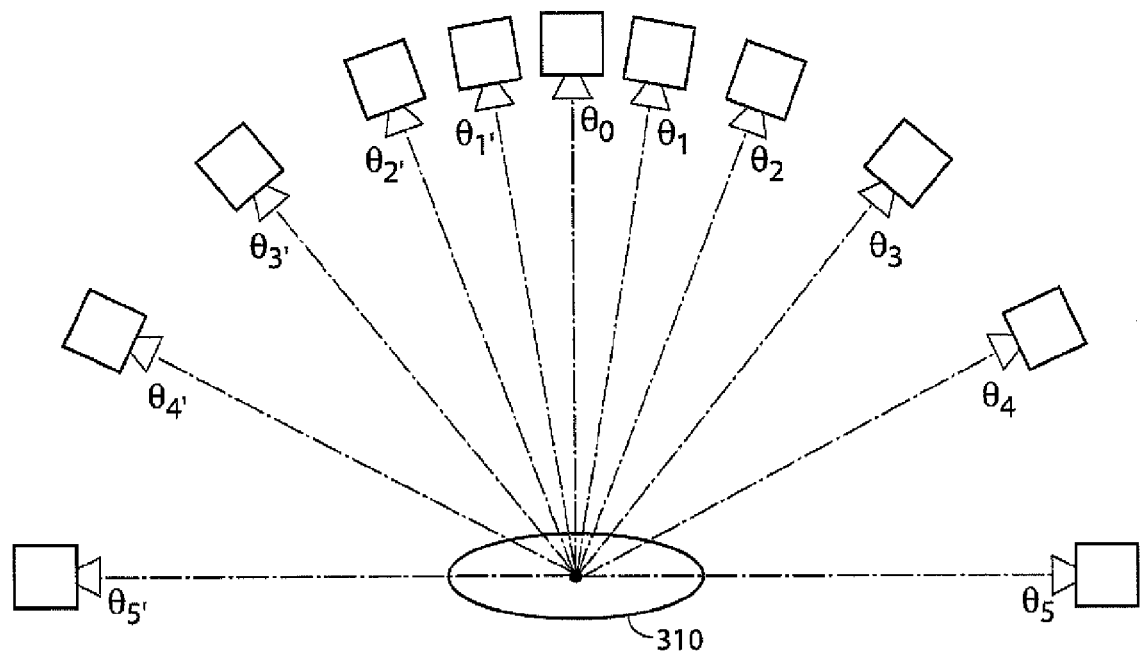
FIGS. 3A and 3B are diagrammatic illustrations of respective exemplary view angle configurations, in accordance with embodiments of the present invention.

In FIG. 3A, the plurality of view angles used to obtain projection data of object 310 are distributed with non-uniform angular offsets with respect to one another. For example, as the view angles are rotated away from a reference view angle at $\theta_0=0°$ in both the clockwise and counterclockwise directions, the angle between each successive view angle increases. In particular, in the clockwise direction $(\theta_1-\theta_0)<(\theta_2-\theta_1)<(\theta_3-\theta_2)$, etc. Similarly, in the counterclockwise direction, $(\theta_{1'}-\theta_0)<(\theta_{2'}-\theta_{1'})<(\theta_{3'}-\theta_{2'})$. As discussed in the '848 patent, performing exposures at non-uniform angles may facilitate obtaining optimal projection data for a given dose budget.

At each of the plurality of view angles, the radiation energy may be varied to compensate for changes in the material thickness of object 310 in directions related to the respective view angle. It should be appreciated that the number and distribution illustrated in FIG. 3A are merely exemplary. Any number of view angles may be used at any desired distribution, as the aspects of the invention are not limited in this respect. Moreover, the view angles need not be distributed symmetrically with respect to the reference view angle, as any desired distribution may be used with the various aspects of the invention.

Figure 3B:
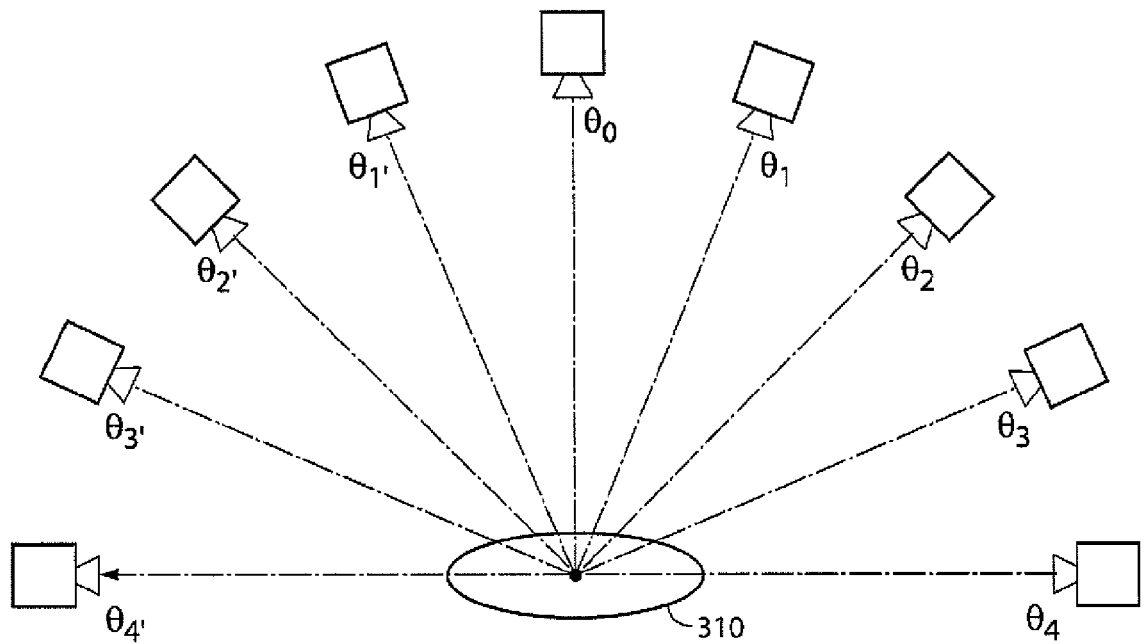

In FIG. 3B, the angular offsets are distributed essentially uniformly about object 310. For example, as the view angles are rotated away from the reference view angle at $\theta_0=0°$ in both the clockwise and counterclockwise directions, the angle between each successive view angle remains essentially the same. In particular, in the clockwise direction, $(\theta_1-\theta_0)=(\theta_2-\theta_1)=(\theta_3-\theta_2)$, etc. Similarly, in the counterclockwise direction, $(\theta_{1'}-\theta_0)=(\theta_{2'}-\theta_{1'})=(\theta_{3'}-\theta_{2'})$. At each of the plurality of view angles, the radiation energy may be varied to compensate for changes in the material thickness of object 310 in directions related to the respective view angle. Accordingly, any number of view angles may be distributed in any fashion; uniformly or non-uniformly, symmetric or asymmetric, etc., as the aspects of the invention are not limited in this respect. In addition, the angular range over which projection data is obtained need not be 180° as illustrated in FIGS. 3A and 3B, but may cover a range greater than or less than 180°.

As discussed above, the relationship in Equation 2 may be used to compute an appropriate radiation energy to be used as a function of material thickness to maintain subject dose within a desired range and/or to maintain sufficient contrast information in radiation exiting the object. Alternatively, the set of radiation energies used for a particular procedure may be determined empirically from information obtained from prior procedures using similar objects, or by taking measurements using phantom objects having material properties similar to the object being imaged. For example, in mammography, experience from prior breast imaging procedures may be used to gain an understanding of the appropriate energy levels for various thicknesses of the breast. Alternatively, phantom objects having material properties similar to the breast may be imaged to determine the appropriate energy levels for various thicknesses through the phantom object.

Once the relationship between thickness and radiation energy has been established for a particular type or class of objects, (either empirically or analytically), measurements of a target object to be imaged may be obtained to design an appropriate exposure plan (i.e., a plan for the number and distribution of view angles and the corresponding radiation energy to be used at each successive view angle) for the target object. Alternatively, the target object need not be measured before performing an imaging procedure on the object, but merely categorized by inspection. For example, the object may be considered to be a member of a particular class of which the approximate thickness of the object at various view angles is known a priori, for example, through prior measurements or knowledge of the object. In mammography, prior knowledge and/or measurements of breast dimensions may be used in place of performing actual measurements on a subject breast. In addition, the apparatus performing the imaging may obtain measurements of the object being imaged.

In one embodiment, an exposure plan (i.e., a plan for exposing the object at various view angles and radiation energies) is determined for multiple categories of objects, for example, small, medium and large breasts and selected and performed on target breasts according to which category the target breast falls within. Accordingly, a discrete set of exposure plans corresponding to each of the defined categories may be programmed, and the appropriate exposure plan selected to image a particular target object. However, the exposure plan may be optimized for each object via measurements or use of other knowledge.

In another embodiment, information obtained from an exposure of an object at a first view angle may be used to determine the radiation energy to be used at a subsequent view angle. For example, analysis of the projection data obtained at one view angle may be used to bootstrap one or more subsequent exposures. Each successive exposure may provide additional information to guide the radiation energy to be used at the next view angle. Thus, the exposure plan may be determined and/or modified during the exposure procedure. The exposure plan for a particular object may be determined in any suitable manner, as the aspects of the invention are not limited in this respect.

Figure 4:
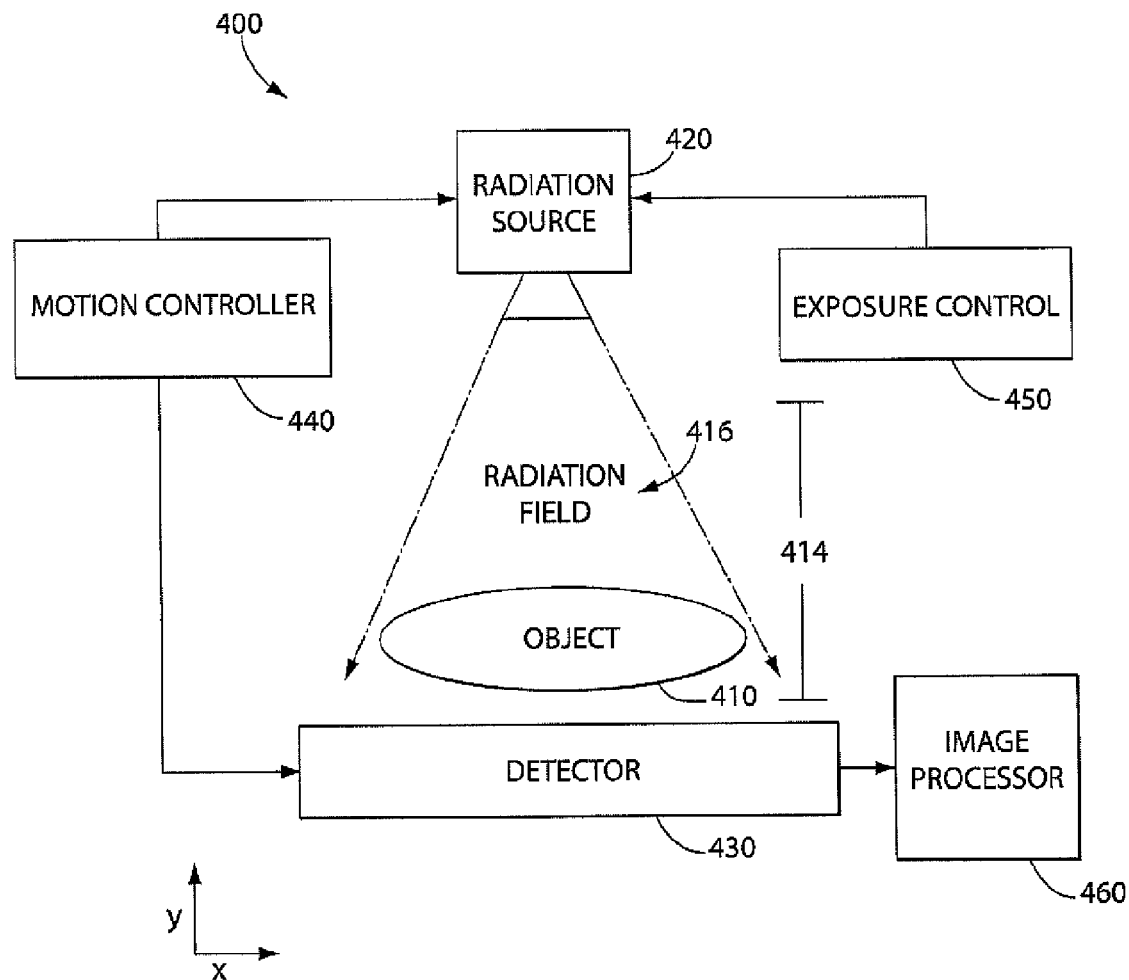
FIG. 4 is a partially block, partially diagrammatic illustration of an imaging system capable of performing methods in accordance with the various aspects of the present invention.

FIG. 4 illustrates one embodiment of an imaging system suitable for obtaining projection data and performing imaging procedures in accordance with various aspects of the present invention. Imaging system 400 includes a radiation source 420, a detector 430, a motion controller 440, a resolution controller 450 and an image processor 460. The imaging system 400 can be used to image a single object 410 or a plurality of objects located within an exposure area 414. The exposure area 414 defines generally the region of space between the radiation source 420 and the detector 430, and is located in the path of the radiation provided by radiation source 420 in the direction of detector 430. The exposure area 414 may be the entire region of space located in the path of the radiation passing from the radiation source 420 to the detector 430, or only a predetermined portion of the space.

Radiation source 420 may be any component or combination of components capable of emitting radiation such as x-ray or gamma radiation. In imaging system 400, radiation source 420 is positioned to emit radiation toward exposure area 414 such that, when object 410 is present in exposure area 414, at least some of the radiation impinges on object 410. In particular, the radiation source 420 is adapted to emit radiation to form a radiation field 416, which may be of any shape or size. In a preferred embodiment, radiation field 416 is formed by a cone beam that substantially encloses object 410 within a cone of x-rays during exposures. However, radiation field 416 may form other shapes such as a fan beam, pencil beam, etc., and may be arranged to expose any portion of object 410, as the aspects of the invention are not limited in this respect.

Radiation source 420 is capable of being rotated about object 410 such that radiation may be directed at object 410 from a plurality of angular positions, i.e., a plurality of view angles with respect to object 410 (e.g., as illustrated in FIGS. 3A and 3B). Detector 430 is positioned to receive at least some of the radiation that passes through the exposure area 414, and in particular, radiation that has penetrated and exited object 410. Detector 430 may be a single detector, or a detector array disposed continuously or at a plurality of discrete locations. Detector 430 may be of any type responsive to radiation generated by radiation source 420. The signals generated by detector 430 carry information about the absorption characteristics of object 410 to form, at least in part, projection data of object 410.

Detector 430 may be configured to rotate in correspondence with the radiation source 420 to detect radiation exiting object 410 from the plurality of view angles. Motion controller 440 may be coupled to radiation source 420 and detector 430 to cause the rotational movement of the radiation source/detector apparatus such that, as the apparatus rotates about the object, the object remains positioned within the exposure area between the source and detector. Motion controller 440 may be capable of being programmed to move the radiation source and detector to any desired view angle with respect to object 410. Together, the radiation source 420, detector 430 and motion controller 440 permit projection data of object 410 to be obtained from any set of view angles. In some embodiments, motion controller 440 may be programmed to control the position of the radiation source and detector independently. For example, the motion controller may move the radiation source and detector along different paths as projection data is obtained from the different view angles, as the aspects of the invention are not limited in this respect.

Exposure control 450 is coupled to radiation source 420 to control the radiation energy of the radiation emitted by the radiation source. As discussed above, the radiation energy emitted from the radiation source may be varied by any suitable means. For example, radiation source 420 may include an x-ray tube adapted to generate an e-beam and direct the e-beam to a target capable of converting e-beam energy to x-ray energy. Exposure control 450 may be coupled to the x-ray tube to control the voltage potential used to generate the e-beam, the magnitude of the voltage being proportional to the energy in the e-beam and, thus, the radiation energy emitted by the target. By controlling the voltage level, exposure control 450 may vary the radiation energy generated by radiation source 420.

Alternatively, radiation source 420 may include one or more filters capable of selectively filtering desired energies from radiation emitted by the radiation source. Accordingly, exposure control 450 may control the one or more filters to vary the energy in the radiation passing through exposure area 414 as desired. Exposure control 450 may also be capable of selecting different materials for the target arranged to convert e-beam energy to x-ray energy. For example, different materials, in response to an impinging e-beam, may convert the e-beam energy to x-ray radiation of differing energy levels. That is, the energy distribution may be a function of target material. Thus, by selectively controlling the target material, exposure control 450 may vary the radiation energy provided by radiation source 420. It should be appreciated that exposure control 450 may be adapted to control the radiation energy emitted by radiation source 420 by any of the above methods, either alone or in any combination. In addition, exposure control 450 may be adapted to control and vary the radiation energy by others means, as the aspects of the invention are not limited in this respect.

Detector 430 may be coupled to image processor 460 to provide the image processor with the projection data generated by exposing the object to radiation at various view angles. Image processor may then reconstruct the projection data into an image of the internal structure of object 410. In one embodiment, a 3D image is computed by image processor 460 from the projection data provided by detector 430. Image processor 460 may include one or more processors and a storage medium capable of storing one or more programs to be executed on the one or more processors. The programs may instruct image processor to process the projection data according to any of various reconstruction algorithms to form images of the structure of the object. Any reconstruction algorithm may be used, as the aspects of the invention are not limited in this respect. For example, image processor 460 may perform any of the reconstruction methods described in the '848 patent, or any other suitable reconstruction scheme capable of transforming projection data into image data. In one embodiment, the relationship in Equation 2 is used to perform reconstruction. Other more complicated relationships may also be used, as the aspects of the invention are not limited in this respect.

In another embodiment, the detector 430 remains stationary as the radiation source is moved about the object. For example, if the detector 430 is sufficiently large (e.g., a flat panel two-dimensional detector array) and/or if the angular range over which projection data is obtained is sufficiently small (e.g., the angular range is limited to a range between 5° and 45° both clockwise and counterclockwise from a reference view angle), a single position for the detector 430 may be sufficient to capture projection data from each of the desired view angles. In addition, in embodiments where detector 430 remains stationary, the object may be positioned in direct contact with the detector.

Imaging system 400 may be used to implement methods according to various aspects of the present invention. For example, the method described in connection with FIG. 2 may be performed on imaging system 400. In particular, motion controller 440 may be configured to rotate radiation source 420 and detector 430 (if appropriate) about object 410 to expose the object to radiation at a plurality of view angles. At each of the plurality of view angles, exposure control 450 may be adapted to select a desired energy level for the radiation emitted by radiation source 420. Accordingly, imaging system 400 may be configured to obtain projection data according to any desired exposure plan.

In other embodiments, radiation may be provided from multiple view angles by a plurality of radiation sources distributed uniformly or non-uniformly about an exposure area to expose an object to be imaged. When it is desired to provide radiation from a particular view angle, the corresponding radiation source may be activated, while the other radiation sources are non-operational. The plurality of radiation sources could be appropriately switched to obtain projection data from view angles defined by the respective stationary positions of the plurality of radiation sources. In such embodiments, the motion controller may be replaced with a controller that successively activates the plurality of radiation sources at desired view angles to obtain projection data of the object positioned in the exposure area.

In embodiments in which a plurality of stationary radiation sources are provided, a corresponding plurality of detector or detector arrays may be positioned to detect radiation emitted by the respective radiation sources. Alternatively, a single detector or detector array positioned to detect radiation emitted by each of the plurality of radiation sources may be used. Other configurations and components capable of providing radiation at a plurality of view angles may be used, as the aspects of the invention are not limited for use on any particular device, or any particular configuration and arrangement of components.

Figure 5:
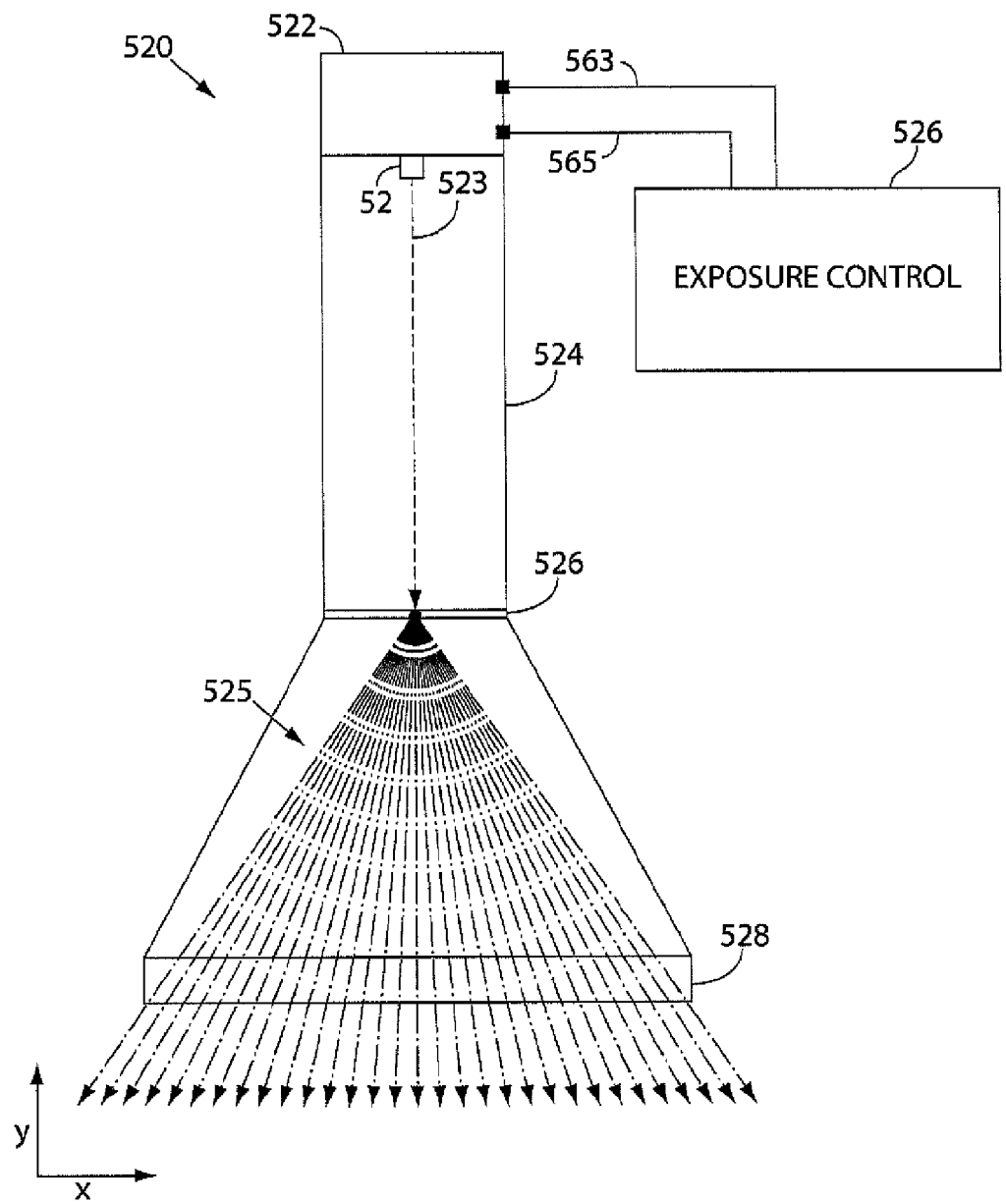
FIG. 5 is an illustration of a method of generating radiation using an x-ray tube and an electron beam (e-beam) focused on a target responsive to the e-beam.

FIG. 5 illustrates an exposure control for a radiation source that produces radiation using e-beam technology, in accordance with one embodiment of the present invention. Radiation source 520 generates an e-beam 523 by forming a voltage potential between a cathode (electron emitting filament 521) and an anode (target material 526). The e-beam propagates through a x-ray tube to impinge on a surface of target 526. As discussed above, the energy in the e-beam is proportional to the voltage potential between the cathode and anode. Radiation in the form of cone beam 525 is emitted as the e-beam strikes the target. Radiation will be emitted having an energy spectrum characteristic of the type of material used and of the energy of the impinging e-beam. In particular, bombarding tungsten with an e-beam will result in a characteristic energy distribution different than bombarding molybdenum, and will vary as a function of the e-beam energy.

Figure 6:
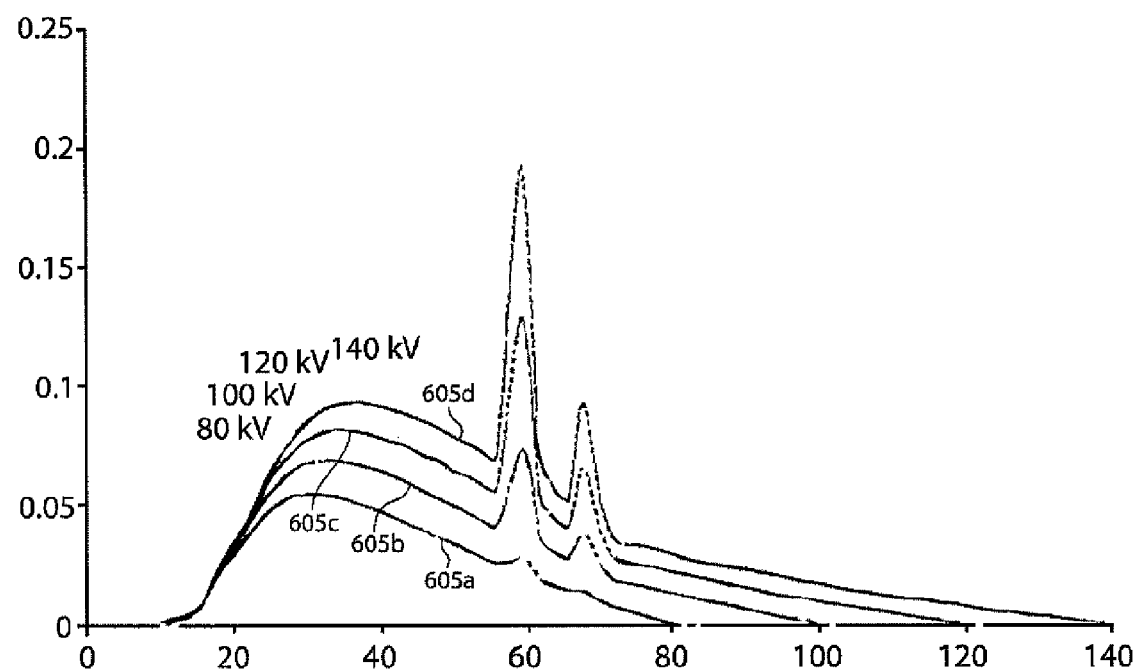
FIG. 6 is an illustration of a typical radiation spectrum obtained as a function of the voltage applied to an x-ray tube.

FIG. 6 illustrates the characteristic spectrum of tungsten at a number of energy levels of an e-beam. In particular, FIG. 6 includes a first spectrum 605a, a second spectrum 605b, a third spectrum 605c, and a fourth spectrum 605d resulting from bombarding a tungsten target with an e-beam generated at a voltage potential of 80 kilo-volts (kV), 100 kV, 120 kV and 140 kV, respectively. The energy spectra illustrated include two components, the Bremsstrahlung radiation, and the energy peaks characteristic of the target material. The Bremsstrahlung radiation is characterized by the generally continuous distribution of radiation that increases in intensity and shifts toward higher frequencies (shorter wavelengths) when the energy of the e-beam is increased. The energy peaks are the characteristic bands shown by the spikes at, for tungsten, approximately 59 kilo-electron volts (keV) and 69 keV. As illustrated, increased e-beam energy increases the intensity of the peaks, but does not shift the peaks to higher frequencies.

As illustrated, the energies in the resulting spectrum of radiation emitted by the target may be controlled, at least in part, by controlling the e-beam energy, which in turn may be controlled via the voltage potential of the x-ray tube. Accordingly, exposure controller 560 may provide a voltage control signal 563 indicative of a desired voltage level of the vacuum tube. The voltage control signal may be received by power and timing control circuitry 522. Power and timing control circuitry 522 may comprise any type of circuitry adapted to modify or establish the voltage potential of the x-ray tube according to voltage control signal 563, thus increasing the energy in e-beam 523. As a result, exposure control 560 is capable of controlling the radiation energy of the radiation emitted from radiation source 520. As indicated by spectrums 605a-605d, the e-beam energy also effects the intensity of the radiation emitted by the target. Accordingly, voltage control signal 563 may also be used to vary the intensity of the radiation provided by radiation source 520.

As discussed above, the radiation intensity of such radiation is related to the number of photons passing through a given volume in a given interval of time (i.e., radiation intensity is a measure of flux). Therefore, the longer radiation source 120 is operated, the more radiation is produced, increasing the radiation intensity (i.e., the more photons that are emitted by the radiation source). Accordingly, radiation intensity may be controlled, at least in part, by controlling how long the radiation source is operated (i.e., by controlling the length of the exposure). Exposure control 560 may provide a timing control signal 565 that indicates the duration of an exposure. For example, timing control signal 565 may be a toggle control that turns the radiation source on and off. Alternatively, timing control signal 565 may be a signal indicative of a duration during which the radiation source should be operated.

The timing control signal 565 may be received by power and timing circuitry 522 to control the length of a given exposure. Power and timing circuitry 522 may include any circuitry adapted to energize and de-energize the radiation source (e.g., power and timing circuitry 522 is capable of turning the radiation source on and off). As a result, exposure control 560 is adapted to control the radiation intensity of radiation emitted by radiation source 520 via the voltage control signal 563, the timing control signal 565, or both.

Exposure control 560 may include one or more processors and a memory capable of storing one or more programs to be executed by the one or more processors. As a result, exposure control may be programmed to control the radiation intensity and radiation energy according to any desired exposure plan. Specifically, exposure control 560 may be programmed to control the exposure parameters of a number of exposures taken from a plurality of view angles to control the subject dose and/or maintain a desired ratio between emitted and exiting radiation that provides suitable contrast.

Radiation source 120 may also include a filter 528 designed to block radiation of particular energies. For example, a filter may be used to suppress one or more of the characteristic peaks of a given target material, or may block some band of energies such that radiation having a more desirable energy spectrum enter an exposure area to impinge on a object being imaged. Filter 528 may be used to further control the energy and/or intensity of the radiation emitted from the radiation source. It should be appreciated that a filter is not required, as the aspects of the invention are not limited in this respect.

As discussed above, various aspects of the present invention may be well suited to performing exposures in relatively low-dose environments. Referring again to FIG. 4, in one embodiment, object 410 is a breast to be imaged in a mammography procedure. When the breast is compressed for imaging, the thickness of the breast material may vary depending on the view angle from which it is viewed. To avoid substantially increasing the subject dose received by the breast at view angles where the thickness of the breast is larger, imaging system 400 may be configured to vary the radiation energy depending on the thickness of the breast at each of a plurality of view angles. As a result, higher energy radiation may be provided to the breast at view angles where increased thicknesses of breast material must be penetrated. As a result, acceptable image quality may be maintained over the range of view angles while limiting the subject dose to safe levels.

In one embodiment, object 410 is a breast that has been compressed in the y-direction in preparation for a mammography procedure. Radiation source 420 may include an x-ray tube and a target, wherein the x-ray tube is adapted to generate an e-beam and direct the e-beam to impinge on a target. Electrons incident on the target, for example, a tungsten target, result in the emission of x-ray radiation. The radiation energy emitted from radiation source 420 may be related to a voltage of the x-ray tube used to generate the electron beam from which the x-ray radiation is formed. According to one exemplary exposure plan, the radiation energy emitted into the exposure area is generated by operating the x-ray tube at a voltage between 20 and 40 Kev when the radiation source is located in substantial alignment with the y-axis (e.g., at position A in FIG. 1) and a voltage between 30 and 90 Kev when the radiation source is located in substantial alignment with the x-axis (e.g., at position C is FIG. 1).

At intermediate angles between position A and position B, the x-rays may be provided at energies resulting from operating the x-ray tube at voltages in between the voltage ranges mentioned above to cause the radiation energy to increase as a function of view angle. It should be appreciated that the above voltage levels are exemplary, and the aspects of the invention are not limited for use with any particular x-ray tube voltage and/or resulting radiation energy distribution. In addition, the radiation energy may be varied in any suitable manner. For example, the x-ray energy may varied by changing the voltage applied to the x-ray tube as discussed above, using different anode material (i.e., providing a target of different materials, each adapted to generate x-ray radiation having different radiation distributions), and/or the use of filters arranged between the source and the object to selectively provide radiation at desired frequencies to the object. The radiation energy may be varied as a function of view angle by any amount and by any means, as the aspects of the invention are not limited in this respect.

In addition, the absorption ratio (i.e., the proportion of radiation impinging on an object that exits the object) may be substantially maintained such that the projection data has contrast sufficient to distinguish the different tissue characteristics within the breast. For example, the ratio of radiation emitted from the radiation source to the radiation penetrating and exiting the breast should be sufficient to distinguish between normal healthy breast tissue and tissue anomalies, particularly with respect to potential cancerous growths in early stages of development. Accordingly, various aspects of the invention facilitate obtaining relatively high contrast volume images, while simultaneously limiting the subject dose received by a patient.

In conventional digital mammography, it was believed necessary to use a nearly flawless detector which covers the entire breast, since flaws or small gaps might contribute to the failure to capture information indicative of a tissue anomaly, for example, an early stage cancer. However, large area flawless detectors are relatively expensive compared to forming a detector to cover a similar area using a number of smaller and/or flawed detectors. In addition, large area detectors are typically flat. Applicant has appreciated that smaller and/or flawed detectors may be combined in an array in a planar or non-planar configuration. Provided that each part of the exposure volume of an object is projected onto a functional part of one of the detectors (i.e., a surface of one of the detectors responsive to the radiation) in at least one exposure (i.e., from at least one view angle), satisfactory projection data may be obtained.

In one embodiment, multiple detectors may be tiled together having small gaps between them to form a detector array (e.g., the detector 430 in FIG. 4). Another embodiment includes forming a detector array using multiple detectors having some insensitive areas that do not provide usable data, but which project to different regions of tissue on each exposure (i.e., at each different view angle). Another embodiment includes disposing the detector array in a non-planar configuration. For example, the multiple detectors can overlap and be arranged in a tilted fashion such that the object (e.g., a breast) may be partially surrounded by the array. However, any number of detectors, in any arrangement, and of any quality may be used, as the aspects of the invention are not limited in this respect.

As discussed in the '848 patent, the subject dose received by a patient may be prevented from exceeding a desired amount by varying the intensity of the radiation emitted by the radiation source with respect to view angle. Applicant appreciated that 3D images could be obtained while operating within a specific dose budget by obtaining relatively high resolution projection data at view angles deemed more critical for the 3D reconstruction, and obtaining lower resolution data at view angles deemed less critical in the 3D reconstruction. For example, in FIG. 3A, the highest radiation intensity may be used at the view angle at $\theta=0°$. As the radiation source rotates about the object in one or both of the clockwise and counterclockwise direction, the radiation intensity may be reduced for each successive view angle.

Applicant has appreciated that benefits of varying the radiation intensity as a function of view angle may also be achieved using exposure plans wherein the view angles are distributed uniformly about the object. For example, variable radiation intensity exposures may be performed using the configuration illustrated in FIG. 3B. In particular, a highest radiation intensity may be used when exposing object 310 from the view angle at $\theta=0°$. As the radiation source rotates about the object in one or both of the clockwise and counter-clockwise direction, the radiation intensity may be reduced for each successive view angle distributed in equiangular offsets from one another. It should be appreciated, however, that variable intensity exposure plans may be used in connection with any number of view angles in any distribution, uniform or non-uniform, as the aspects of the invention are not limited in this respect.

Applicant has further appreciated that concepts related to variable radiation intensity and variable radiation energy exposures may be combined to obtain projection data facilitating the reconstruction of 3D images, while respecting dose budgets designed for imaging sensitive objects such as human tissue and/or for routine imaging procedures where limiting dose may be desirable or even necessary. In particular, a exposure plan may be designed to expose an object at a desired number of view angles. From one view angle to the next, one or both of the radiation intensity and radiation energy may be varied to obtain dose limited projection data.

It should be appreciated that the above described concepts may be used in other combinations, as the aspects of the invention are not limited in this respect.

Applicant provides below additional embodiments of and various concepts related to aspects of the present invention. It should be appreciated that the aspects of the invention are not limited by the embodiments described below. In addition, the various embodiments described below may be used alone or in combination with any of the concepts, features, and/or embodiments described in the foregoing.

For many applications, including diagnostic applications, it is desirable to obtain the best possible quality three dimensional (3D) image of an object while minimizing the exposure of the object. For example, in x-ray screening mammography, it would be desirable to obtain 3D images of the breast, but because exams may be performed on an annual basis, it is desirable that the x-ray dose provided to a patient be minimized so as not to substantially increase the patient's risk of developing breast cancer during that patient's lifetime.

Methods have been disclosed for obtaining generally low-dose images of an object, including the methods described in U.S. Pat. No. 6,744,848 ('848) entitled "Method and System for Low-dose Three-dimensional Imaging of a Scene" and U.S. Pat. No. 5,872,828 ('828) entitled "Tomosynthesis System for Breast Imaging," both of which are herein incorporated by reference in their entirety. In some of the methods described, a small number of two dimensional (2D) images (e.g., between 9 and 30 images) are taken of the object from different view angles. In the '828 patent, each of the images are taken at equal x-ray doses (e.g., obtained at equal energy and flux) and the different view angles are equally spaced from one another. In the '848 patent it was disclosed that the images do not need to be equally spaced and that the provided x-ray flux can be varied between images acquired from the different view angles.

Applicant describes herein additional methods to obtain images (e.g., 3D images) of an object at relatively low dose. These methods include, but are not limited to: methods for varying the x-ray energy; the use of density fiducials; and methods to determine the relationship between observed x-ray intensity and specimen density. While any combination of these methods can be used to obtain a high quality 3D image, each of these methods can also be used independently. These methods may be used either alone or in any combination with methods described in either the '848 or '828 patents.

I. X-ray Intensity to Density Relationship

In transmission x-ray tomographic data processing, a three dimensional specimen density volume is calculated from measurements of the transmitted x-ray intensity along paths from an x-ray source, thru the specimen volume, to an x-ray detector (x-ray projection measurements, referred to herein as projection data). Various methods disclosed below may more accurately model the density from x-ray intensity data (e.g., from the projection data obtained by the x-ray detector).

To reconstruct a three dimensional specimen volume from the x-ray projection measurements, the intensity of the x-ray projection measurements may need to be associated with the density of the specimen. For un-scattered monochromatic x-rays this relationship may be modeled by exponential absorption along the x-ray path. This relatively simple relationship between projection measurements and specimen density is complicated, however, by a number of factors including: spectrum of the x-ray source; beam-hardening by the specimen; and x-ray scatter by the specimen.

X-ray Source Energy Distribution. The x-ray source in most imaging applications is typically not monochromatic, but instead has a more complicated polychromatic spectrum.

The source can also be filtered to preferentially remove x-rays, for example, the low energy x-rays, to more closely approximate a monochromatic x-ray source. Further complicating the intensity-density relationship is the fact that the x-ray dose (i.e., by varying the x-ray flux) provided by the x-ray source may be intentionally varied as a function of the view angle as described, for example, in the '848 patent.

X-ray scatter. Measured x-ray intensity values for a given x-ray path is both reduced by scatter away from the initial x-ray paths from the x-ray source and increased by scatter from other x-ray paths to a given detection point.

Beam Hardening. Beam hardening refers to effect of the spread of energy in a polychromatic x-ray source. In particular, as a polychromatic x-ray beam travels through a specimen, lower energy x-rays will be preferentially absorbed by the specimen. As a result, density at the proximal side of the specimen will receive a different x-ray energy distribution than density at the distal side.

Together, scattered x-rays and beam hardening may be substantial causes of inaccurate projected density calculations in conventional 3D imaging method (for example the Tomosynthesis method described in the '828). These inaccurate projected density calculations cause error artifacts in the reconstructed 3D images. Both scattering and beam-hardening increase the intensity recorded at the detector for any given projected density, although the effects differ for higher density projections. Some aspects of the invention are directed to accounting, at least in part, for these effects.

In one embodiment a set of projections of a breast is obtained using either a same or different radiation energy without using density fiducials. An initial 3D reconstruction is calculated using, for example, the methods described in the '848 patent and/or the '828 patent. This initial reconstruction is then used to provide a density model of the breast to calculate beam scatter and absorption based on the known x-ray energy distribution for each projection as well as the absorption/scatter characteristics of the breast. A second reconstruction is then performed utilizing this information.

In another embodiment, a subset of the projections is collected with an anti-scatter grid, while the remaining projections are collected without the anti-scatter grid. The resulting sets of projection data may (or may not) be at the same angular positions and may (or may not) be at the same x-ray exposure. In one example, low dose pre-exposures of the first, middle and last angles in the tomographic sequence are acquired with an anti-scatter grid. By comparing a projection data obtained with an anti scatter grid with the projection data acquired for the tomographic reconstruction, the ratio of scatter to transmitted x-rays can be estimated over the whole of the image. By doing this for multiple source positions of the tomographic sequence, such as the extremes of the angular range and the mid-position, the ratio of scatter to transmitted x-ray intensity can be interpolated for other angles in the sequence.

In another embodiment, the relationship between x-ray intensity and density can be estimated from the different projected tissue thickness from rays at different angles. Because of beam hardening and intentional variation of the x-ray energy between exposures, the same volume of density will be exposed to a different x-ray energy distribution as a function of the view angle. By comparing the derived density updates from data collected at different view angles (and therefore different penetration depths) the intensity-density ratio can be further defined.

In a further embodiment, the relationship between x-ray intensity and density may be estimated from projection data where exposures from some view angles are taken more than once, repeated exposures being performed using different x-ray energies. The comparison of the projection data taken with different energies can be used to determine the relative absorption coefficients of the tissue for the various x-ray energies. Since the scattering of the tissue varies with energy, the comparison can also be used to estimate the contribution of scattered x-rays to the detected intensity. The exposure for the comparison energies need not be the same, since the images can be scaled. In a variant on the method, very low dose images can be used for these comparisons.

II. Density Fiducials

In another embodiment, projection data is obtained from a plurality of exposures having one or more density fiducials arranged in an exposure area during respective exposures. In one application of density fiducials, the fiducials are used to provide information useful in calculating specimen density from observed x-ray intensity information. This information can be used alone to facilitate characterizing scatter and/or beam hardening effects, or in combination with methods described above as a check of the corresponding method. Preferably, information provided by one or more density fiducials is also used to refine the reconstruction either during or post calculation of one or more images.

In one embodiment, one or more density fiducials arranged in the exposure area are selected from a range of densities and x-ray absorption properties similar to the object being imaged. In one example, for a breast imaging application, the one or more density fiducial has a density in a range of densities spanning from 75% to 200% of the density of the prevalent fatty tissue. The one or more density fiducials may be placed such that, in each exposure, there will be a set of fiducials on both sides of the object (i.e., arranged proximal and distal relative to the x-ray source.) In one breast imaging example, one ore more fiducials can be attached to modified compression paddles used to compress and generally immobilize the breast.

In another embodiment, one or more fiducials may be placed above or below the compression paddles such that the shadow of the one or more fiducials moves across the specimen as a function of the imaging position. Since radiation will encounter a fiducial located proximally relative to the source before interacting with the object being imaged such that the fidicial will not absorb x-rays scattered by the object that are directed towards the detector, the intensity variation due to the shadow from a fiducial proximal to the x-ray source will differ from the shadow caused by a similar fiducial placed distally with respect to the radiation source. In particular, the component of intensity due to scatter from breast tissue outside of the shadow of the fiducial will be unaffected by the fiducial proximal to the source. Thus, the difference between the two shadows may be used to measure the contribution of the scattered x-rays to the intensity measured by the detector.

Shadows from fiducials that do not intersect with the object may be used to calibrate the relationship between absorption and projected density by direct measurement; for this purpose the projection of the fiducial must be taken into account; spherical fiducials are useful since the projected density is dependent only on the angle of x-ray incidence on the detector. In the case that the x-ray energy is varied between exposures, this direct information is may be particularly useful.

In another embodiment, one or more density fiducials arranged in an exposure area are opaque or substantially opaque to the x-ray beam. In this case, x-ray intensity observed under the shadow of the one or more fiducials can be considered to be from x-ray scatter. This allows the direct determination of the effect of x-ray scatter. If opaque fiducials are employed, it may be desirable to position the fiducials between the specimen and the x-ray source and substantially above the specimen such that the shadow of one or more fiducials does not occlude the same region of the specimen as the specimen is imaged from different view angles. As an alternative, the position of the one or more fiducials may be moved between exposures at the different view angles. It should be appreciated that in the above examples, the fiducials may either be moved relative to the specimen, for example, by moving the fiducials with the x-ray source and/or detector, or may be located at a fixed position relative to specimen.

In evaluating if one or more fiducials should be placed proximal or distal to the specimen, consideration may be given to the fact that fiducials placed proximal to the specimen provide information without x-ray exposure to the specimen, whereas fiducials placed distal to the specimen interrupt at least some x-rays that have already traveled through the specimen.

The proportionate reduction in intensity by a density fiducial can be measured by comparing the mean of the intensity in pixels shadowed by the fiducial with the mean intensity of nearby pixels not shadowed by the fiducial. For a fiducial of known density variation, the intensity variation may be measured as a function of the projected fiducial density. Alternatively, the edge of the fiducial shadow can be examined; the median or mean ratio of x-ray intensity change across the edge of the shadow of the density fiducial can be measured.

While scatter affects, amongst other things, the high density asymptote of the density-intensity relationship, beam hardening affects, amongst other things, the curvature of the relationship. The proportionate difference in intensity for a small increment in density of a density fiducial provided information about the local slope of the intensity-density relationship, whereas the effect of a density fiducial with a high increment in density provides information about the intensity recorded for high densities, which will differ according to the location of the density fiducial with respect to the specimen (as discussed above).

In another application of the use of fiducials, the observed location of the fiducials can be used to refine the geometry of the imaging apparatus. For a variety of reasons, including user error and the uncertainty in the mechanical positioning of the apparatus, the imaging geometry might not be precisely known from a simple readout of the component positions. Information from one or more fiducials can be used as a method to check and to refine the imaging geometry.

III. Identification of Specimen Boundaries

The accuracy of the calculation of the density distribution may be enhanced by the identification of the specimen boundaries. In many cases, a portion of the surface boundaries can be determined from the imaging geometry. For example, in breast imaging, the breast is often constrained by a compression device. This allows precise determination of the regions of the breast that are in contact with the compression device. In this example, however, a significant portion of the surface boundary can not be determined in this manner. If this surface is not correctly determined, the reconstruction algorithms may inappropriately place density either inside or outside the specimen boundaries. This may lead to reconstruction errors at the skin line in iterative and non-iterative algorithms. In one embodiment of the present invention, additional x-ray exposures may be taken from source positions further out from the chest wall. In another embodiment, additional x-ray exposures are performed at higher angles. In both the previous embodiments, the additional x-ray exposures may be taken at respective lower x-ray doses than taken in the one or more main exposures.

In another embodiment, skin surface information is collected using x-ray absorbing markers placed on the skin surface. These x-ray absorbing markers could also serve as density fiducials as mentioned above. The markers could be placed on the skin either directly (e.g. using a mesh garment or tape), or indirectly using an inflatable pillow (or pillows) attached to the compression paddle, the pillows could be on either the proximal paddle or the distal paddle, or both paddles. In evaluating if such pillows should be placed proximal or distal to the specimen, consideration may be given to the fact that a pillow placed proximal to the specimen provides information without x-ray exposure to the specimen, whereas a pillow placed distal to the specimen will be interrupting x-rays that have already traveled through the specimen. Filling such pillows with fluid with an x-ray density similar to breast tissue may mitigate the effect of the surface boundary upon the reconstruction algorithms.

In another embodiment, the pillow could be filled with fluid and have a surface with structures such as corrugations or capsules which hold spaces filled with lower density material (e.g. air) next to the skin. These spaces could serve as markers for the skin surface. Pillows may be inflated either before or after compression of the breast is established. Inflation after compression may help to prevent the pillow from interfering with the compression procedure.

In another embodiment, specimen boundary information may be collected optically. For example, in 3D breast imaging by projecting a grid pattern onto the skin between the compression paddles, and imaging the pattern with one camera close to the x-ray source, and one positioned close to the detector. In another example, two or more optical images of the specimen may be taken and standard surface mapping techniques that employ the use of feature recognition and/and texture mapping can be used to identify the surface boundaries. Once the specimen boundaries are identified, the reconstruction algorithms can assign regions outside the specimen the correct background density (typically 0 for air).

IV. Pre-exposures to Estimate Imaging Properties

In addition to the uses described above, low dose pre-exposures may be used to estimate various imaging properties and to assist in the identification of problems that occur during the collection of image data. Low dose pre-exposures can be used for determining specimen or subject motion by comparing the images with the actual tomographic image acquisition. Such pre exposures also allow for automatic energy and dose exposure compensation, since the dose used for the actual tomographic image acquisition can be adjusted on the basis of the pre exposure images. A common problem in mammography is poor patient positioning. By using data such as the height, weight, age of the patient in combination with the angles and thickness from the compression system, low dose images can be examined to ascertain the position of the pectoral muscle and the extent of coverage of breast tissue. This information can be automatically used to alert the operator to the need to reposition the patient. Determining inadequate positioning before the main exposure sequence is often valuable in locations where the cases are not evaluated immediately, since a patient call back for a repeated exam might be avoided. Furthermore, in combination with the techniques described above for detecting the skin line of the specimen, the common problem in which a part of the specimen overlaps the edge of the detector can be anticipated and the operator automatically alerted.

V. Detecting Specimen Motion

Specimen motion can be identified based on two or more images taken at the same position (e.g., from the same view angle). Preferably, images are taken at the start and end of the imaging procedure. Well known image mathematics (in particular, cross-correlation or image difference methods) can be employed to detect or determine any specimen motion. This information can be automatically used to alert the operator to the need to repeat the exposure, or to omit or correct some data during the computational reconstruction process. In various embodiments described above, two or more images are acquired at the same view angle (e.g., the exposures may be repeated at the same view angle) to allow an improved estimate of the intensity to density relationship. When those methods are employed, it is possible to use resulting images to detect specimen motion. It should be appreciated, though, that repeating an exposure at a particular view angle may be repeated solely for the purposes of detecting specimen motion, or in combination with other techniques.

VI. Display Resolution

The resolution of reconstructed volumes in typically not uniform, and differs according to the orientation of features in the tissue. In addition, there are artifacts due to the reconstruction algorithms which can be misleading. Because of these issues it may be important to only display tissue structures that are well determined by the data. In one embodiment of this invention, the plane to plane resolution of the reconstructed image is limited for display purposes to a predetermined resolution (e.g., from 3 to 5 mm) between planes to assist in preventing spurious structures from being displayed to the radiologist, while still displaying the full resolution within the plane. In another embodiment of the present invention, the display allows tilting the displayed volume, but limits this tilt to a range of angles less than the angular range used for the x-ray source motion.

Displaying Information on a Display Device with Lower Resolution than the Data

The medical community often uses very high resolution monitors to ensure that every pixel from the data may be displayed. It is sometimes necessary to produce lower resolution images from higher resolution data. Often averaging is used to combine the information from multiple data pixels into a single display pixel. However, for some imaging applications such as mammography, this may be inadequate. In particular, mammographic images may contain sharp features such as microcalcifications which may be diagnostically important. Averaging techniques may render these features less conspicuous. Applicant has recognized that combining the pixels by recording a maximum pixel value instead of the average pixel value may improve the conspicuity of such small, bright features. Alternatively, Applicant has recognized that averaging techniques may be used after applying a function to adjust the relative influence of pixels with different intensities. After averaging, the inverse function may be applied to recover the original pixel value scaling.

Displaying Information from Multiple Planes

In order to display information from more than a single plane simultaneously, maximum intensity projection has been suggested ("Tomographic mammography using a limited number of low-dose cone-beam projection images," Wu et al, Med Phys 30 (3), March 2003). Maximum intensity projection has the disadvantage that features can be completely hidden by slightly denser features which project to the same displayed pixels. To mitigate this effect, Applicant has appreciated that the radiologist is typically not interested in visualizing the densities pertaining to fat, the projection can be calculated as a standard average along rays but applying a function to the density data before projection. The function adjusts the relative influence of pixels with different values projecting to the same average pixel. After averaging, the inverse function may be applied to recover the original pixel value scaling. A further aspect of this invention is that such projections be rapid in order to enable interactive control by the user.

Another issue in displaying multiple planes in projection is that features which fall outside of the range of planes projected for display may be clinically important. An example of this is the clustering of microcalcifications. If there is a sharp boundary to the range of planes projected for display then some microcalcifications may be invisible, and the clustering may be misunderstood. To avoid this effect, in one embodiment, the contribution from planes at and near the boundary of the range of planes projected for display is gently tapered instead of having a sharp cutoff. This tapering causes features such as Microcalcifications to brighten and dim with distance in a more intuitive manner as the projection range of planes projected for display is swept through the 3D data.

It should be appreciated that while various embodiments described herein have focused primarily on x-ray imaging, the methods disclosed here can also be applied to other imaging modalities, such as optical imaging, IR imaging, PECT, SPECT and gamma imaging, and NMR and ultrasound imaging. Further, while many of the examples were provided for breast imaging, these methods may also be employed for any imaging applications (including non-medical imaging applications) where it is useful to minimize either the x-ray dose provided to the specimen or the image acquisition time. Further, the methods used to evaluate the intensity-density relationship may be applied to conventional imaging modalities, such as the various forms of both high-dose and low-dose CT imaging.

Following below are descriptions of various embodiments of methods and apparatus according to the present invention. It should be appreciated that various aspects of the invention described herein may be implemented in any of numerous ways. Examples of specific implementations are provided herein for illustrative purposes only. In addition, the various aspects of the invention described in the embodiments below may be used alone or in any combination, and are not limited to the combinations explicitly described herein.

One embodiment includes a method of imaging an object comprising the acts of irradiating the object from a plurality of angular positions using a plurality of different x-ray energies, detecting radiation transmitted through the object at each angular position, producing two-dimensional transmission data representative of the radiation transmitted through the object at each of the plurality of angular positions, and producing a three-dimensional image of the object based on said two-dimensional x-ray data.

Another embodiment includes a method of imaging an object comprising the acts of irradiating the object from a plurality of non-uniformly distributed angular positions using a plurality of different x-ray energies, detecting radiation transmitted through the object at each angular position, producing two-dimensional transmission data representative of the radiation transmitted through the object at each of the plurality of non-uniformly distributed angular positions, and producing a three-dimensional image of the object based on said two-dimensional x-ray data.

Another embodiment includes a method of imaging an object comprising the acts of irradiating the object from a plurality of uniformly distributed angular positions using a plurality of different x-ray doses, detecting radiation transmitted through the object at each angular position, producing two-dimensional transmission data representative of the radiation transmitted through the object at each of the plurality of uniformly distributed angular positions, and producing a three-dimensional image of the object based on said two-dimensional x-ray data.

Another embodiment includes a method of imaging an object comprising the acts of irradiating the object from a plurality of uniformly or non-uniformly distributed angular positions, detecting radiation transmitted through the object at each angular position, producing two-dimensional transmission data representative of the radiation transmitted through the object at each of the plurality of uniformly or non-uniformly distributed angular positions, producing a preliminary three-dimensional image of the object based on said two-dimensional x-ray data, using said preliminary three-dimensional image of the object to derive a model of x-ray scatter from the object, and calculating a final three-dimensional image of the object based on the two-dimensional x-ray and the model of the x-ray scatter.

Another embodiment includes a method of imaging an object comprising the acts of irradiating the object from a plurality of uniformly or non-uniformly distributed angular positions, detecting radiation transmitted through the object at each angular position, producing two-dimensional transmission data representative of the radiation transmitted through the object at each of the plurality of uniformly or non-uniformly distributed angular positions, producing a preliminary three-dimensional image of the object based on said two-dimensional x-ray data, using said preliminary three-dimensional image of the object to derive a model of x-ray beam hardening from the object, and calculating a final three-dimensional image of the object based on the two-dimensional x-ray and the model of the x-ray beam hardening.

Another embodiment includes a method of imaging an object comprising the acts of irradiating the object from a plurality of uniformly or non-uniformly distributed angular positions, detecting radiation transmitted through the object at each angular position, producing two-dimensional transmission data representative of the radiation transmitted through the object at each of the plurality of uniformly or non-uniformly distributed angular positions, producing a preliminary three-dimensional image of the object based on said two-dimensional x-ray data, using said preliminary three-dimensional image of the object to derive a model of x-ray beam hardening and x-ray scattering from the object, and calculating a final three-dimensional image of the object based on the two-dimensional x-ray and the model of the x-ray beam hardening and x-ray scatter.

Another embodiment includes a method of imaging an object comprising the acts of irradiating the object from a plurality of uniformly or non-uniformly distributed angular positions, wherein a subset of said angular positions employ an anti-scatter grid, detecting radiation transmitted through the object at each angular position, producing two-dimensional transmission data representative of the radiation transmitted through the object at each of the plurality of uniformly or non-uniformly distributed angular positions, producing a three-dimensional image of the object based on said two-dimensional x-ray data in which differences between the images collected with and without the anti-scatter grid is used to incorporate x-ray scatter corrections.

Another embodiment includes a method of imaging an object comprising the acts of irradiating the object from a plurality of uniformly or non-uniformly distributed angular positions, detecting radiation transmitted through the object at each angular position, producing two-dimensional transmission data representative of the radiation transmitted through the object at each of the plurality of uniformly or non-uniformly distributed angular positions, producing a three-dimensional image of the object based on said two-dimensional x-ray data in which differences between the images collected at each of the plurality positions, each which passes through a different thickness of the object, is used to calculate the effect of beam hardening on the x-ray intensity to density relationship.

Another embodiment includes a method of imaging an object comprising the acts of irradiating the object from a plurality of uniformly or non-uniformly distributed angular positions, wherein a subset of the angular positions are imaged two or more times, each time at a different x-ray energy, detecting radiation transmitted through the object at each angular position, producing two-dimensional transmission data representative of the radiation transmitted through the object at each of the plurality of uniformly or non-uniformly distributed angular positions, producing a three-dimensional image of the object based on said two-dimensional x-ray data in which differences between the images collected at the same position is used to refine the intensity to density relationship.

Another embodiment includes a method of imaging an object comprising the acts of placing density fiducials between the x-ray source and the object, irradiating the object from a plurality of uniformly or non-uniformly distributed angular positions, detecting radiation transmitted through the object at each angular position, producing two-dimensional transmission data representative of the radiation transmitted through the object at each of the plurality of uniformly or non-uniformly distributed angular positions, producing a three-dimensional image of the object based on said two-dimensional x-ray data in which information derived from the density fiducials is used to refine the x-ray intensity to density relationship.

Another embodiment includes a method of imaging an object comprising the acts of placing density fiducials between the object and the x-ray detector, irradiating the object from a plurality of uniformly or non-uniformly distributed angular positions, detecting radiation transmitted through the object at each angular position, producing two-dimensional transmission data representative of the radiation transmitted through the object at each of the plurality of uniformly or non-uniformly distributed angular positions, producing a three-dimensional image of the object based on said two-dimensional x-ray data in which information derived from the density fiducials is used to refine the x-ray intensity to density relationship.

Another embodiment includes a method of imaging an object comprising the acts of placing density fiducials both between the object and the x-ray source and between the x-ray detector, irradiating the object from a plurality of uniformly or non-uniformly distributed angular positions, detecting radiation transmitted through the object at each angular position, producing two-dimensional transmission data representative of the radiation transmitted through the object at each of the plurality of uniformly or non-uniformly distributed angular positions, producing a three-dimensional image of the object based on said two-dimensional x-ray data in which information derived from the density fiducials is used to refine the x-ray intensity to density relationship.

Another embodiment includes a method of imaging an object comprising the acts of placing density fiducials between the x-ray source and the object, wherein the density of said fiducials spans the range from 75% to 150% of the predominant density in the object, irradiating the object from a plurality of uniformly or non-uniformly distributed angular positions, detecting radiation transmitted through the object at each angular position, producing two-dimensional transmission data representative of the radiation transmitted through the object at each of the plurality of uniformly or non-uniformly distributed angular positions, producing a three-dimensional image of the object based on said two-dimensional x-ray data in which information derived from the density fiducials is used to refine the x-ray intensity to density relationship.

Another embodiment includes a method of imaging an object comprising the acts of placing density fiducials between the object and the x-ray detector, wherein the density of said fiducials spans the range from 75% to 150% of the predominant density in the object, irradiating the object from a plurality of uniformly or non-uniformly distributed angular positions, detecting radiation transmitted through the object at each angular position, producing two-dimensional transmission data representative of the radiation transmitted through the object at each of the plurality of uniformly or non-uniformly distributed angular positions, producing a three-dimensional image of the object based on said two-dimensional x-ray data in which information derived from the density fiducials is used to refine the x-ray intensity to density relationship.

Another embodiment includes a method of imaging an object comprising the acts of placing density fiducials both between the object and the x-ray source and between the x-ray detector, wherein the density of said fiducials spans the range from 75% to 150% of the predominant density in the object, irradiating the object from a plurality of uniformly or non-uniformly distributed angular positions, detecting radiation transmitted through the object at each angular position, producing two-dimensional transmission data representative of the radiation transmitted through the object at each of the plurality of uniformly or non-uniformly distributed angular positions, producing a three-dimensional image of the object based on said two-dimensional x-ray data in which information derived from the density fiducials is used to refine the x-ray intensity to density relationship.

Another embodiment includes a method of imaging an object comprising the acts of placing density fiducials between the x-ray source and the object, wherein the density of said fiducials is greater than 150% of the predominant density in the object, irradiating the object from a plurality of uniformly or non-uniformly distributed angular positions, detecting radiation transmitted through the object at each angular position, producing two-dimensional transmission data representative of the radiation transmitted through the object at each of the plurality of uniformly or non-uniformly distributed angular positions, producing a three-dimensional image of the object based on said two-dimensional x-ray data in which information derived from the density fiducials is used to refine the x-ray intensity to density relationship.

Another embodiment includes a method of imaging an object comprising the acts of placing density fiducials between the object and the x-ray detector, wherein the density of said fiducials is greater than 150% of the predominant density in the object, irradiating the object from a plurality of uniformly or non-uniformly distributed angular positions, detecting radiation transmitted through the object at each angular position, producing two-dimensional transmission data representative of the radiation transmitted through the object at each of the plurality of uniformly or non-uniformly distributed angular positions, producing a three-dimensional image of the object based on said two-dimensional x-ray data in which information derived from the density fiducials is used to refine the x-ray intensity to density relationship.

Another embodiment includes a method of imaging an object comprising the acts of placing density fiducials both between the object and the x-ray source and between the x-ray detector, wherein the density of said fiducials is greater than 150% of the predominant density in the object, irradiating the object from a plurality of uniformly or non-uniformly distributed angular positions, detecting radiation transmitted through the object at each angular position, producing two-dimensional transmission data representative of the radiation transmitted through the object at each of the plurality of uniformly or non-uniformly distributed angular positions, producing a three-dimensional image of the object based on said two-dimensional x-ray data in which information derived from the density fiducials is used to refine the x-ray intensity to density relationship.

Another embodiment includes a method of imaging an object comprising the acts of placing density fiducials between the x-ray source and the object, wherein the density of said fiducials spans the range from 75% to 150% of the predominant density in the object, irradiating the object from a plurality of uniformly or non-uniformly distributed angular positions, detecting radiation transmitted through the object at each angular position, producing two-dimensional transmission data representative of the radiation transmitted through the object at each of the plurality of uniformly or non-uniformly distributed angular positions, producing a three-dimensional image of the object based on said two-dimensional x-ray data in which information derived from the density fiducials is used to refine the imaging geometry.

Another embodiment includes a method of imaging an object comprising the acts of placing density fiducials between the object and the x-ray detector, wherein the density of said fiducials spans the range from 75% to 150% of the predominant density in the object, irradiating the object from a plurality of uniformly or non-uniformly distributed angular positions, detecting radiation transmitted through the object at each angular position, producing two-dimensional transmission data representative of the radiation transmitted through the object at each of the plurality of uniformly or non-uniformly distributed angular positions, producing a three-dimensional image of the object based on said two-dimensional x-ray data in which information derived from the density fiducials is used to refine the imaging geometry.

Another embodiment includes a method of imaging an object comprising the acts of placing density fiducials both between the object and the x-ray source and between the x-ray detector, wherein the density of said fiducials spans the range from 75% to 150% of the predominant density in the object, irradiating the object from a plurality of uniformly or non-uniformly distributed angular positions, detecting radiation transmitted through the object at each angular position, producing two-dimensional transmission data representative of the radiation transmitted through the object at each of the plurality of uniformly or non-uniformly distributed angular positions, producing a three-dimensional image of the object based on said two-dimensional x-ray data in which information derived from the density fiducials is used to refine the imaging geometry.

Another embodiment includes a method of imaging an object comprising the acts of placing density fiducials between the x-ray source and the object, wherein the density of said fiducials is greater than 150% of the predominant density in the object, irradiating the object from a plurality of uniformly or non-uniformly distributed angular positions, detecting radiation transmitted through the object at each angular position, producing two-dimensional transmission data representative of the radiation transmitted through the object at each of the plurality of uniformly or non-uniformly distributed angular positions, producing a three-dimensional image of the object based on said two-dimensional x-ray data in which information derived from the density fiducials is used to refine the imaging geometry.

Another embodiment includes a method of imaging an object comprising the acts of placing density fiducials between the object and the x-ray detector, wherein the density of said fiducials is greater than 150% of the predominant density in the object, irradiating the object from a plurality of uniformly or non-uniformly distributed angular positions, detecting radiation transmitted through the object at each angular position, producing two-dimensional transmission data representative of the radiation transmitted through the object at each of the plurality of uniformly or non-uniformly distributed angular positions, producing a three-dimensional image of the object based on said two-dimensional x-ray data in which information derived from the density fiducials is used to refine the imaging geometry.

Another embodiment includes a method of imaging an object comprising the acts of placing density fiducials both between the object and the x-ray source and between the x-ray detector, wherein the density of said fiducials is greater than 150% of the predominant density in the object, irradiating the object from a plurality of uniformly or non-uniformly distributed angular positions, detecting radiation transmitted through the object at each angular position, producing two-dimensional transmission data representative of the radiation transmitted through the object at each of the plurality of uniformly or non-uniformly distributed angular positions, producing a three-dimensional image of the object based on said two-dimensional x-ray data in which information derived from the density fiducials is used to refine the imaging geometry.

Another embodiment includes a method of imaging an object comprising the acts of irradiating the object from a plurality of uniformly or non-uniformly distributed angular positions, detecting radiation transmitted through the object at each angular position, collecting two or more optical images of the object, producing two-dimensional transmission data representative of the radiation transmitted through the object at each of the plurality of uniformly or non-uniformly distributed angular positions, producing a three-dimensional image of the object based on said two-dimensional x-ray data in which information derived from the two or more optical images is used to determine the object boundaries.

Another embodiment includes a method of imaging an object comprising the acts of irradiating the object from a plurality of uniformly or non-uniformly distributed angular positions, detecting radiation transmitted through the object at each angular position, collecting two or more optical images of the object, wherein optically identifiable features are projected onto the object, producing two-dimensional transmission data representative of the radiation transmitted through the object at each of the plurality of uniformly or non-uniformly distributed angular positions, producing a three-dimensional image of the object based on said two-dimensional x-ray data in which information derived from the two or more optical images is used to determine the object boundaries.

Another embodiment includes a method of imaging an object comprising the acts of placing x-ray opaque markers on the surface of the object, irradiating the object from a plurality of uniformly or non-uniformly distributed angular positions, detecting radiation transmitted through the object at each angular position, producing two-dimensional transmission data representative of the radiation transmitted through the object at each of the plurality of uniformly or non-uniformly distributed angular positions, producing a three-dimensional image of the object based on said two-dimensional x-ray data in which information derived from the x-ray opaque markers is used to determine the object boundaries.

Another embodiment includes a method of imaging an object comprising the acts of placing the object within a flexible material that conforms to the boundaries of the object and has a known outer boundary, wherein the flexible material has a density less than the object, irradiating the object from a plurality of uniformly or non-uniformly distributed angular positions, detecting radiation transmitted through the object at each angular position, producing two-dimensional transmission data representative of the radiation transmitted through the object at each of the plurality of uniformly or non-uniformly distributed angular positions, producing a three-dimensional image of the object based on said two-dimensional x-ray data.

Another embodiment includes a method of imaging an object comprising the acts of placing the object within a flexible material that conforms to the boundaries of the object and has a known outer boundary, wherein the flexible material has a density approximately equal to that of the object, irradiating the object from a plurality of uniformly or non-uniformly distributed angular positions, detecting radiation transmitted through the object at each angular position, producing two-dimensional transmission data representative of the radiation transmitted through the object at each of the plurality of uniformly or non-uniformly distributed angular positions, producing a three-dimensional image of the object based on said two-dimensional x-ray data.

Another embodiment includes a method of imaging an object comprising the acts of placing the object within a flexible material that conforms to the boundaries of the object and has a known outer boundary, wherein the flexible material has a density greater than that of the object, irradiating the object from a plurality of uniformly or non-uniformly distributed angular positions, detecting radiation transmitted through the object at each angular position, producing two-dimensional transmission data representative of the radiation transmitted through the object at each of the plurality of uniformly or non-uniformly distributed angular positions, producing a three-dimensional image of the object based on said two-dimensional x-ray data.

Another embodiment includes a method of imaging an object comprising the acts of irradiating the object from a plurality of uniformly or non-uniformly distributed angular positions, wherein a set of pre-exposures are collected at a subset of the angular positions, detecting radiation transmitted through the object at each angular position, producing two-dimensional transmission data representative of the radiation transmitted through the object at each of the plurality of uniformly or non-uniformly distributed angular positions, producing a three-dimensional image of the object based on said two-dimensional x-ray data, wherein differences between the pre-exposure data and the exposure data is used to determine if the object moved as the set of images was being collected.

Another embodiment includes a method of imaging an object comprising the acts of irradiating the object from a plurality of uniformly or non-uniformly distributed angular positions, wherein a set of pre-exposures are collected at a subset of the angular positions, detecting radiation transmitted through the object at each angular position, producing two-dimensional transmission data representative of the radiation transmitted through the object at each of the plurality of uniformly or non-uniformly distributed angular positions, producing a three-dimensional image of the object based on said two-dimensional x-ray data, wherein differences between the pre-exposure data and the exposure data is used to refine the x-ray intensity to density model.

Another embodiment a method of imaging an object comprising the acts of irradiating the object from a plurality of uniformly or non-uniformly distributed angular positions, wherein a set of pre-exposures are collected at a subset of the angular positions, detecting radiation transmitted through the object at each angular position, producing two-dimensional transmission data representative of the radiation transmitted through the object at each of the plurality of uniformly or non-uniformly distributed angular positions, producing a three-dimensional image of the object based on said two-dimensional x-ray data, wherein gaps or missing data in said two-dimensional x-ray data are identified and data from these regions are not used in the calculation of the three-dimensional image.

Another embodiment a method of displaying a three-dimensional image of an object in which the display resolution is limited to the imaging resolution generated by the three-dimensional imaging method.

Another embodiment a method of displaying a three-dimensional image of an object in which only the maximum pixel value from each sub-region of the three-dimensional image is displayed.

Another embodiment includes a method of displaying a three-dimensional image of an object in which a scaled difference of the maximum pixel value and the average pixel value from each sub-region of the three-dimensional image is displayed.

As mentioned above, the foregoing additional embodiments of and various concepts related to aspects of the present invention. The additional embodiments may be used alone or in combination with any other method, technique or embodiment described herein, as the aspects of the invention are not limited to the particular combination described herein.

The above-described embodiments of the present invention can be implemented in any of numerous ways. For example, the embodiments may be implemented using hardware, software or a combination thereof. When implemented in software, the software code can be executed on any suitable processor or collection of processors, whether provided in a single computer or distributed among multiple computers. It should be appreciated that any component or collection of components that perform the functions described above can be generically considered as one or more controllers that control the above-discussed function. The one or more controller can be implemented in numerous ways, such as with dedicated hardware, or with general purpose hardware (e.g., one or more processor) that is programmed using microcode or software to perform the functions recited above.

It should be appreciated that the various methods outlined herein may be coded as software that is executable on one or more processors that employ any one of a variety of operating systems or platforms. Additionally, such software may be written using any of a number of suitable programming languages and/or conventional programming or scripting tools, and also may be compiled as executable machine language code.

In this respect, it should be appreciated that one embodiment of the invention is directed to a computer readable medium (or multiple computer readable media) (e.g., a computer memory, one or more floppy discs, compact discs, optical discs, magnetic tapes, etc.) encoded with one or more programs that, when executed on one or more computers or other processors, perform methods that implement the various embodiments of the invention discussed above. The computer readable medium or media can be transportable, such that the program or programs stored thereon can be loaded onto one or more different computers or other processors to implement various aspects of the present invention as discussed above.

It should be understood that the term "program" is used herein in a generic sense to refer to any type of computer code or set of instructions that can be employed to program a computer or other processor to implement various aspects of the present invention as discussed above. Additionally, it should be appreciated that according to one aspect of this embodiment, one or more computer programs that when executed perform methods of the present invention need not reside on a single computer or processor, but may be distributed in a modular fashion amongst a number of different computers or processors to implement various aspects of the present invention.

Various aspects of the present invention may be used alone, in combination, or in a variety of arrangements not specifically discussed in the embodiments described in the foregoing and is therefore not limited in its application to the details and arrangement of components set forth in the foregoing description or illustrated in the drawings. The invention is capable of other embodiments and of being practiced or of being carried out in various ways. In particular, the various concepts related to variable radiation energy and variable radiation intensity may be used in any way, either alone or in any combination, as the aspects of the invention are not limited to the specific combinations described herein. Accordingly, the foregoing description and drawings are by way of example only.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

What is claimed is:

1. A mammography method of imaging a breast by obtaining projection data of the breast from a plurality of view angles with respect to the breast, the method comprising acts of:
   determining a dose budget safe for breast imaging, the dose budget defining a maximum amount of radiation allowable to be absorbed by the breast during imaging;
   providing radiation, at each of the plurality of view angles, to an exposure area in which the breast is positioned;
   controlling a radiation energy of the radiation provided at each of the plurality of view angles such that the respective radiation energy is varied depending on a thickness of the breast at each of the respective plurality of view angles such that a sum of radiation absorbed by the breast over all of the plurality of view angles does not exceed the dose budget;
   detecting at least some of the radiation passing through the object at each of the plurality of view angles to obtain the projection data; and
   reconstructing the projection data to form at least one image of the breast.

2. The method of claim 1, wherein the thickness is based on at least one of measurements obtained from the breast and a model of the breast based on prior experience and/or measurements obtained from similar breasts.

3. The method of claim 1, wherein the act of selecting the radiation energy includes acts of increasing the radiation energy as a result of an increase in the thickness of the breast and decreasing the radiation energy as a result of a decrease in the thickness of the breast in a direction related to the respective view angle.

4. The method of claim 1, wherein the act of providing the radiation includes an act of providing the radiation from a radiation source having an x-ray tube including an operating voltage related to the radiation energy emitted from the radiation source, the method further comprising an act of modifying the operating voltage to vary the radiation energy provided by the radiation source.

5. The method of claim 1, further comprising an act of filtering the radiation emitted by the radiation source to selectively modify the radiation energy provided at the respective plurality of view angles.

6. The method of claim 1, wherein each of the plurality of view angles are selected such tat an offset angle between successive view angles is uniform for each of the plurality of view angles.

7. The method of claim 1, wherein each of the plurality of view angles are selected such that an offset angle between successive view angles is non-uniform for at least two pairs of adjacent view angles.

8. The method of claim 7, wherein the plurality of view angles include a reference view angle, and wherein the offset angle between successive view angles increases as an angle between a given view angle and the reference view angle increases.

9. The method of claim 1, further comprising an act of controlling a radiation intensity of the radiation provided at each of the plurality of view angles such that the radiation intensity is different for at least two of the plurality of view angles.

10. The method of claim 1, wherein the radiation includes x-ray radiation.

11. The method of claim 1, wherein the object is a human female breast, the method further comprising an act of compressing the breast such that the breast has a first thickness along a first axis that is smaller than a second thickness along a second axis, and wherein the act of controlling the radiation energy includes an act of selecting generally higher radiation energies for radiation provided at view angles more closely aligned with the second axis than radiation energies selected for radiation provided at view angles more closely aligned with the first axis such that the dose budget is not exceeded during imaging.

12. A mammography apparatus for imaging a breast by obtaining projection data of the breast from a plurality of view angles with respect to the breast, the apparatus configured to image the breast according to a predetermined dose budget safe for breast imaging, the dose budget defining the maximum amount of radiation allowable to be absorbed by the breast during imaging, the apparatus comprising:

a radiation source adapted to provide radiation to an exposure area in which the breast may be positioned, the radiation source being moveable to provide the radiation to the exposure area from each of the plurality of view angles;

an exposure controller coupled to the radiation source, the exposure controller adapted to control a radiation energy of the radiation provided by the radiation source at each of the plurality of view angles such that the respective radiation energy is varied depending on a thickness of the breast at each of the respective plurality of view angles;

a memory, coupled to the exposure controller, storing at least one exposure plan, the at least one exposure plan indicating a radiation energy to be used at each of the plurality of view angles such that a sum of radiation absorbed by the breast does not exceed the dose budget;

at least one detector positioned to detect at least some of the radiation passing through the object at each of the plurality of view angles to obtain the projection data; and an image processor to reconstruct at least one image of the breast from the projection data.

13. The apparatus of claim 12, wherein the expected thickness is based on at least one of measurements obtained from the breast and a model of the breast based on prior experience and/or measurements obtained from similar breasts.

14. The apparatus of claim 12, wherein the exposure controller is configured to increase the radiation energy when a thickness of the breast increases in a direction related to the respective view angle.

15. The apparatus of claim 12, wherein the radiation source includes an x-ray tube having an operating voltage related to the radiation energy of the radiation provided by the radiation source, and wherein the exposure controller is adapted to control the radiation energy of the radiation provided at each of the plurality of view angles by controlling the operating voltage of the x-ray tube.

16. The method of claim 12, wherein each of the plurality of view angles are selected such that an offset angle between successive view angles is uniform for each of the plurality of view angles.

17. The method of claim 12, wherein each of the plurality of view angles are selected such that an offset angle between successive view angles is non-uniform for at least two pairs of adjacent view angles.

18. The apparatus of claim 17, wherein the plurality of view angles include a reference view angle, and wherein the offset angle between successive view angles increases as an angle between a given view angle and The reference view angle increases.

19. The apparatus of claim 15, wherein the exposure controller is further adapted to control a radiation intensity of the radiation provided by the radiation source at each of the plurality of view angles such that the respective radiation intensity is different for at least two of the plurality of view angles.

20. The apparatus of claim 19, wherein the operating voltage of the x-ray tube is related to the radiation intensity provided by the radiation source, and wherein the exposure controller is configured to vary the radiation intensity by controlling the operating voltage.

21. The apparatus of claim 19, wherein the exposure controller is configured to vary the radiation intensity by controlling a length of an exposure interval during which the x-ray tube is operating at each of the plurality of view angles.

22. The apparatus of claim 19, further comprising a motion controller adapted to position the radiation source at each of the plurality of view angles.

23. The apparatus of claim 22, wherein the motion controller and exposure controller may be configured to automatically control the apparatus to obtain the projection data according to the exposure plan.

24. The apparatus of claim 22, wherein the apparatus is a mammography apparatus adapted to obtain projection data of a breast, the mammography apparatus further comprises compression plates configured to position and compress the breast such that the breast has a first thickness along a first axis that is smaller than a second thickness along a second axis, and wherein the exposure controller is adapted to select generally higher radiation energies for radiation provided at view angles more closely aligned with the second axis than radiation energies selected for radiation provided at view angles more closely aligned with the first axis.

* * * * *